US012290346B2

(12) United States Patent
Shapiro

(10) Patent No.: US 12,290,346 B2
(45) Date of Patent: *May 6, 2025

(54) MOTION ARTIFACT REMOVAL BY TIME DOMAIN PROJECTION

(71) Applicant: Apple Inc., Cupertino, CA (US)

(72) Inventor: Ian R. Shapiro, Saratoga, CA (US)

(73) Assignee: Apple Inc., Cupertino, CA (US)

( * ) Notice: Subject to any disclaimer, the term of this patent is extended or adjusted under 35 U.S.C. 154(b) by 848 days.

This patent is subject to a terminal disclaimer.

(21) Appl. No.: 16/983,700

(22) Filed: Aug. 3, 2020

(65) Prior Publication Data
US 2020/0359919 A1 Nov. 19, 2020

Related U.S. Application Data

(63) Continuation of application No. 14/454,562, filed on Aug. 7, 2014, now Pat. No. 10,758,133.

(51) Int. Cl.
A61B 5/024 (2006.01)
A61B 5/00 (2006.01)
A61B 5/026 (2006.01)

(52) U.S. Cl.
CPC .......... A61B 5/02416 (2013.01); A61B 5/721 (2013.01); A61B 5/02405 (2013.01); A61B 5/0261 (2013.01)

(58) Field of Classification Search
CPC .............. A61B 5/721; A61B 5/02416
See application file for complete search history.

(56) References Cited

U.S. PATENT DOCUMENTS 5,483,261 A   1/1996   Yasutake
5,488,204 A   1/1996   Mead et al.
(Continued)

FOREIGN PATENT DOCUMENTS

JP   2000163031   6/2000
JP   2002342033   11/2002

OTHER PUBLICATIONS

Asada et al., "Active Noise Cancellation Using MEMS Accelerometers for Motion-Tolerant Wearable Bio-Sensors," Proceedings of the 26th Annual International Conference of the IEEE EMBS, 2004, pp. 2157-2160.

(Continued)

Primary Examiner — Amelie R Davis
(74) Attorney, Agent, or Firm — Brownstein Hyatt Farber Schreck, LLP

(57) ABSTRACT

An algorithm for removing motion artifacts from the PPG signal in the time domain to determine heart rate is disclosed. A device for determining a heart rate of a user can include a heart rate sensor configured to generate heart rate signals when positioned on or adjacent to a user's skin, an accelerometer configured to generate one or more acceleration signals, and processing circuitry configured to remove, in a time domain, motion artifacts from the heart rate signals based on the acceleration signals. In some examples, the removal of motion artifacts can also be based on mean-centered, variance-scaled integrated acceleration signals. In some examples, the processing circuitry can be configured to remove motion artifacts using a least squares algorithm to identify a best representation of acceleration and integrated acceleration signals in the heart rate signals.

14 Claims, 15 Drawing Sheets

(56) References Cited

U.S. PATENT DOCUMENTS

| | | |
|---|---|---|
| 5,825,352 A | 10/1998 | Bisset et al. |
| 5,835,079 A | 11/1998 | Shieh |
| 5,880,411 A | 3/1999 | Gillespie et al. |
| 6,188,391 B1 | 2/2001 | Seely et al. |
| 6,310,610 B1 | 10/2001 | Beaton et al. |
| 6,323,846 B1 | 11/2001 | Westerman et al. |
| 6,690,387 B2 | 2/2004 | Zimmerman et al. |
| 7,015,894 B2 | 3/2006 | Morohoshi |
| 7,184,064 B2 | 2/2007 | Zimmerman et al. |
| 7,663,607 B2 | 2/2010 | Hotelling et al. |
| 8,479,122 B2 | 7/2013 | Hotelling et al. |
| 2002/0165471 A1 | 11/2002 | Halperin |
| 2004/0142496 A1* | 7/2004 | Nicholson ............ A61B 5/7264 436/536 |
| 2004/0186387 A1* | 9/2004 | Kosuda ................ A61B 5/721 600/502 |
| 2005/0101889 A1* | 5/2005 | Freeman ............. A61H 31/007 601/41 |
| 2006/0197753 A1 | 9/2006 | Hotelling |
| 2011/0066042 A1 | 3/2011 | Pandia |
| 2012/0016253 A1* | 1/2012 | Koh .................... A61B 5/721 600/534 |
| 2012/0065524 A1 | 3/2012 | Morren |
| 2012/0108928 A1* | 5/2012 | Tverskoy ............ A61B 5/0059 600/324 |
| 2013/0109592 A1 | 5/2013 | Fan |
| 2013/0190903 A1 | 7/2013 | Balakrishnan |
| 2014/0275854 A1 | 9/2014 | Venkatraman |
| 2015/0374300 A1 | 12/2015 | Najarian |
| 2016/0000335 A1* | 1/2016 | Khachaturian ........ G06V 20/40 600/476 |
| 2016/0038045 A1 | 2/2016 | Shapiro |
| 2017/0128019 A1* | 5/2017 | Shao .................... A61B 5/0015 |

OTHER PUBLICATIONS

Lee, et al., "A Multi-Touch Three Dimensional Touch-Sensitive Tablet," Proceedings of CHI: ACM Conference on Human Factors in Computing Systems, Apr. 1985, pp. 21-25.

Rubine, "The Automatic Recognition of Gestures," CMU-CS-91-202, Submitted in Partial Fulfillment of the Requirements for the Degree of Doctor of Philosophy in Computer Science at Carnegie Mellon University, Dec. 1991, 285 pages.

Rubine, "Combining Gestures and Direct Manipulation," CHI '92, May 1992, pp. 659-660.

Sameni, "A Deflation Procedure for Subspace Decomposition," IEEE Transactions on Signal Processing, vol. 58, No. 4, Apr. 2010, pp. 2363-2374.

Westerman, "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 1999, 364 pages.

* cited by examiner

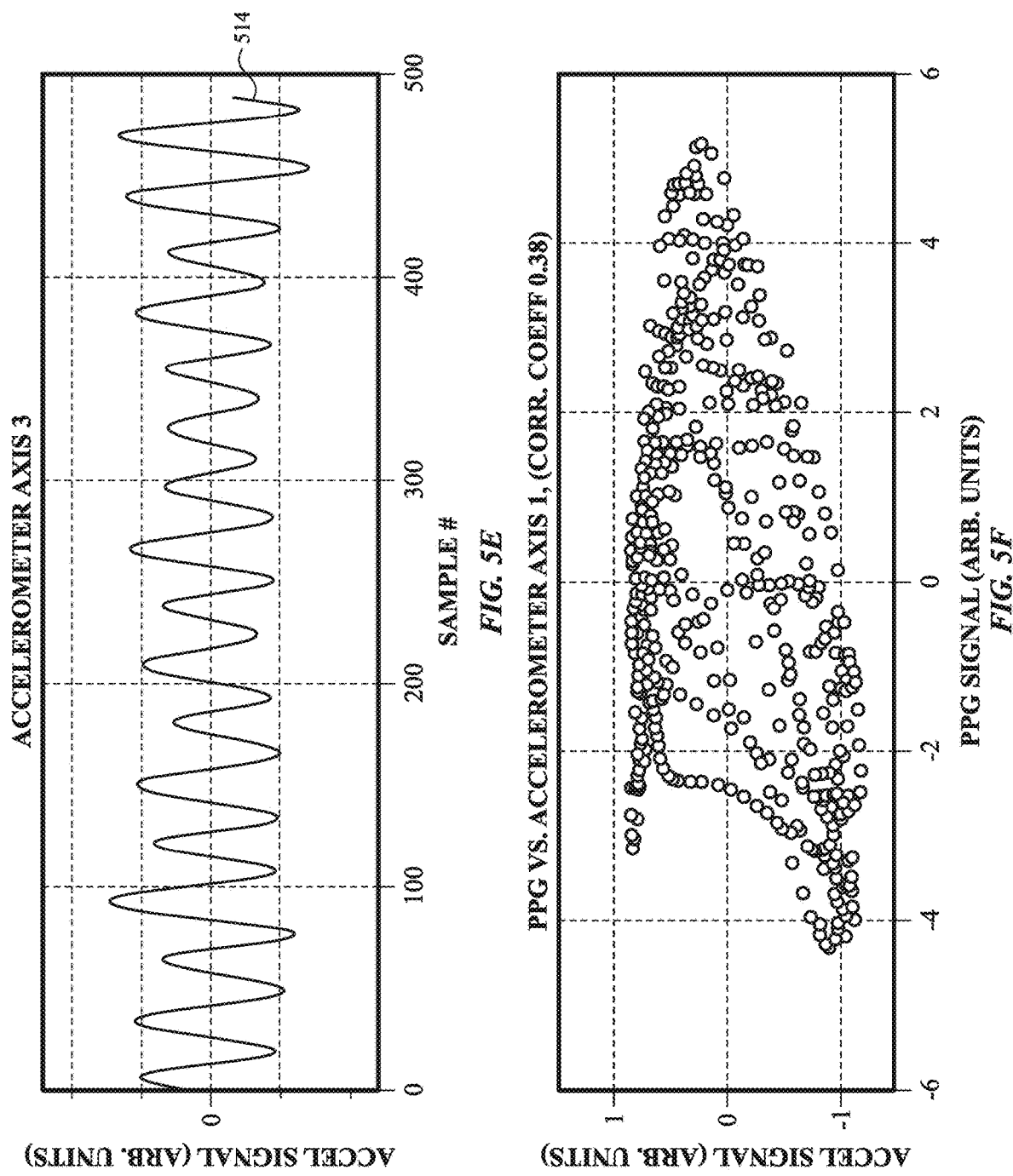

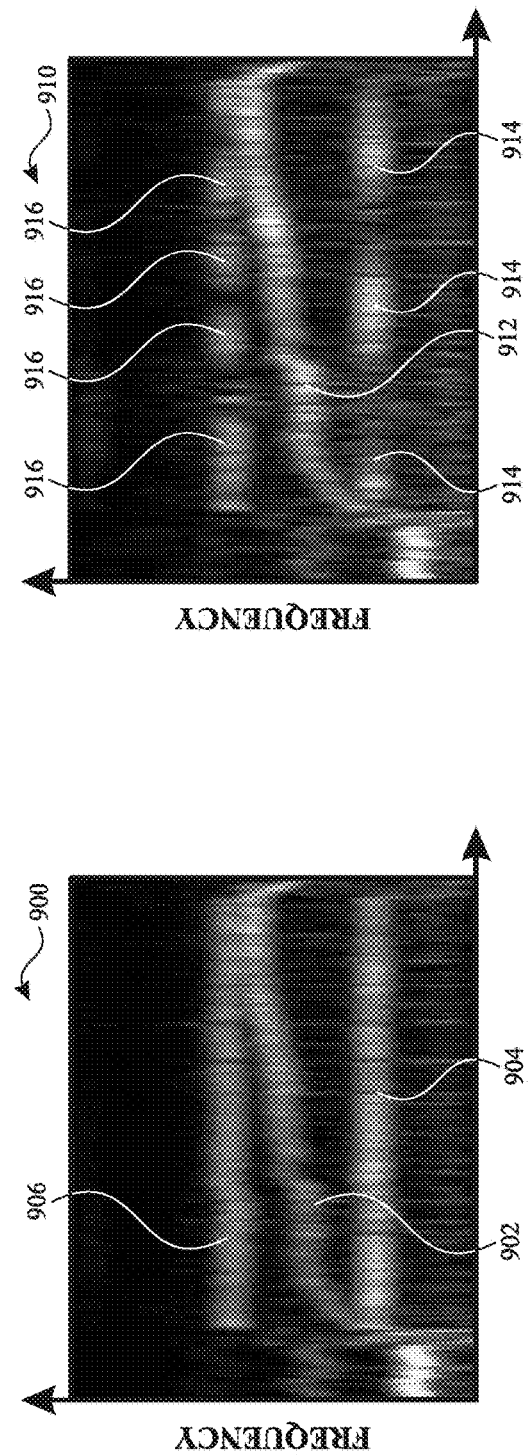
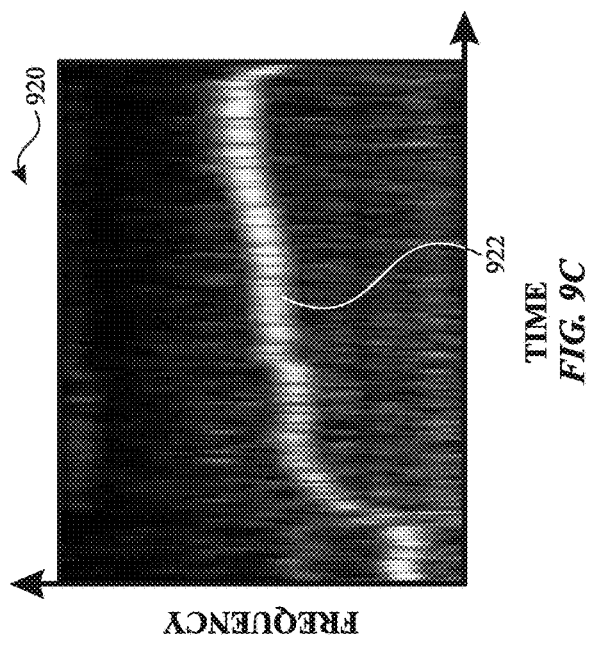
FIG. 9A
FIG. 9B
FIG. 9C

MOTION ARTIFACT REMOVAL BY TIME DOMAIN PROJECTION

This application is a continuation of U.S. patent application Ser. No. 14/454,562, filed on Aug. 7, 2014, the contents of which are incorporated by reference as if fully disclosed herein.

FIELD OF THE DISCLOSURE

This relates generally to processing of a photoplethysmogram (PPG) signal and, more specifically, to removing motion artifacts from the PPG signal in the time domain to determine heart rate.

BACKGROUND OF THE DISCLOSURE

A photoplethysmogram (PPG) signal can be obtained from a pulse oximeter, which employs a light emitter and a light sensor to measure the perfusion of blood to the skin of a user. The PPG signal can be compromised by noise due to motion (e.g., acceleration) artifacts. That is, movement of the body of a user can cause the skin and vasculature to expand and contract, introducing acceleration artifacts into the PPG signal. As a result, motion artifacts can make it difficult to effectively determine a user's heart rate.

BRIEF SUMMARY OF THE DISCLOSURE

This relates to removing motion artifacts from the PPG signal in the time domain to determine heart rate. A device for determining a heart rate of a user can include a heart rate sensor configured to generate heart rate signals when positioned on or adjacent to a user's skin, an accelerometer configured to generate one or more acceleration signals, and processing circuitry configured to remove, in a time domain, motion artifacts from the heart rate signals based on the acceleration signals. In some examples, the removal of motion artifacts can also be based on mean-centered, variance-scaled integrated acceleration signals. In some examples, the processing circuitry can be configured to remove motion artifacts using a least squares algorithm to identify a best representation of acceleration and integrated acceleration signals in the heart rate signals.

BRIEF DESCRIPTION OF THE DRAWINGS

FIGS. 9A through 9C illustrate spectrograms of PPG signals before and after removing motion artifacts according to examples of the disclosure.

DETAILED DESCRIPTION OF THE DISCLOSURE

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

A photoplethysmogram (PPG) signal can be obtained from a pulse oximeter, which employs a light emitter and a light sensor to measure the perfusion of blood to the skin of a user. However, the signal can be compromised by noise due to motion artifacts especially artifacts caused by acceleration. That is, movement of the body of a user can cause the skin and vasculature to expand and contract, introducing noise to the signal. To address the presence of motion artifacts, examples of the present disclosure utilize an accelerometer to measure movements of the user and signal processing of the PPG signal in combination with the accelerometer signal to remove unwanted artifacts in the time domain. For example, a device for determining a heart rate of a user can include a heart rate sensor configured to generate heart rate signals when positioned on or adjacent to a user's skin, an accelerometer configured to generate one or more acceleration signals, and processing circuitry configured to remove, in a time domain, motion artifacts from the heart rate signals based on the acceleration signals. In some examples, the removal of motion artifacts can also be based on mean-centered, variance-scaled integrated acceleration signals. In some examples, the processing circuitry can be configured to remove motion artifacts using a least squares algorithm to identify a best representation of acceleration and integrated acceleration signals in the heart rate signals.

Figure 1:
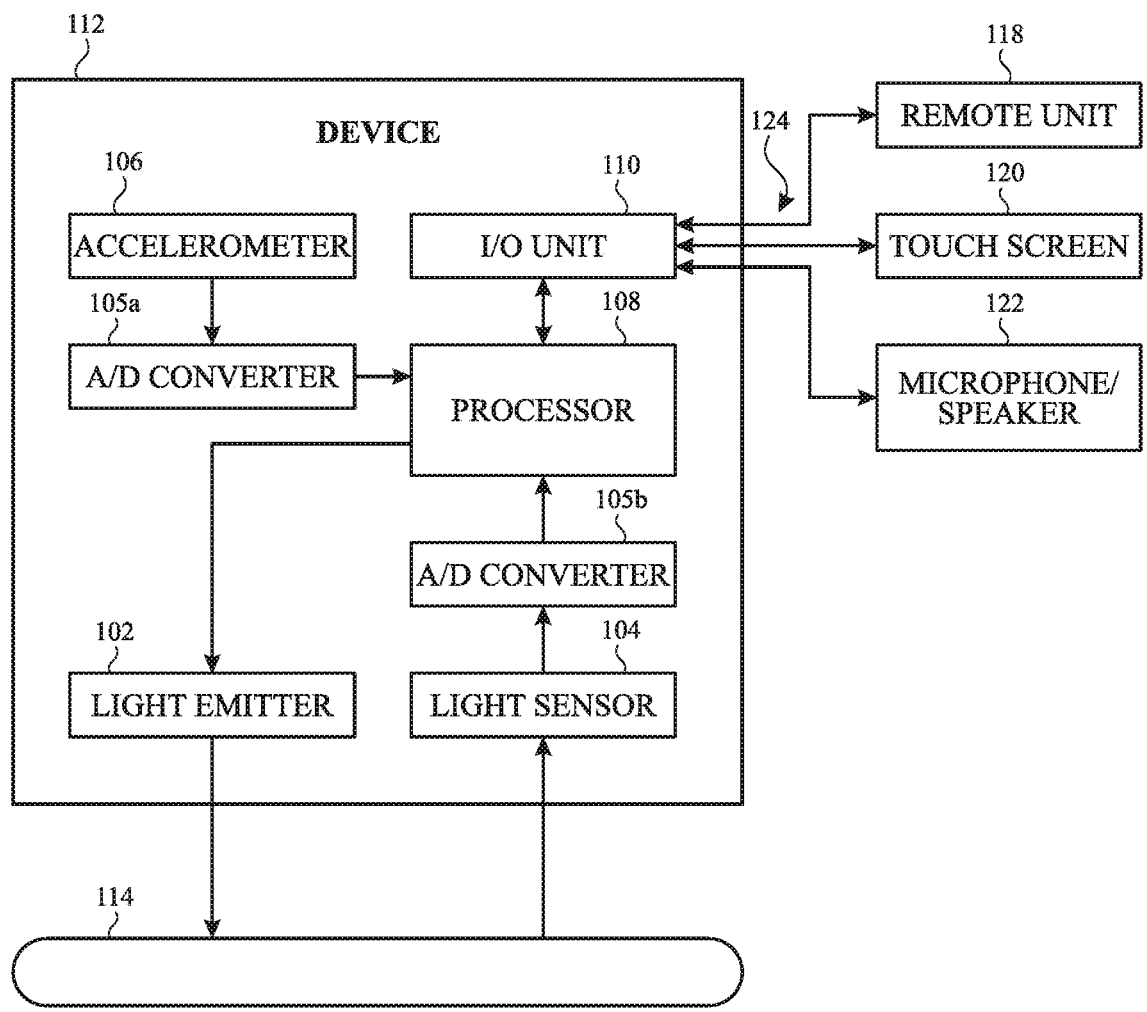
FIG. 1 illustrates an exemplary block diagram of a system for removing motion artifacts in the time domain according to examples of the disclosure.

FIG. 1 illustrates an exemplary block diagram of a system for removing motion artifacts in the time domain according to examples of the disclosure. As illustrated in FIG. 1, the block diagram can include a light emitter 102, light sensor 104, analog-to-digital converters (ADCs) 105a and 105b, accelerometer 106, processor 108 and input/output (I/O) unit 110. These components can be incorporated within a physical device 112 that can be worn or held by a user so as to secure the device to a user's skin (a limb for example) or otherwise attached to an article of clothing worn by the user, with the light emitter 102 and light sensor 104 positioned proximate to a user's skin. Alternately, the device 112 can be entirely or partially incorporated within a smartphone or other portable device such that a user can hold the smartphone in a manner to cause the below described light beam to be reflected from the user's skin back into a light sensor positioned within the smartphone itself. A portion of the light from light emitter 102 can be absorbed by the skin, vasculature, and/or blood, among other possibilities, and a portion can be reflected back to a light sensor 104 co-located with the light emitter. The signals from the sensor 104 can include heart rate signals due to the blood pulse wave.

Although illustrated in FIG. 1 as having only a single light emitter 102 and light sensor 104, in other examples multiple channels can be used in the system. The multiple channels can be created by increasing the number of emitter/sensor pairs, where each emitter/sensor pair can create a new channel, for example. In other examples, multiple channels can be created using different light paths from one emitter to multiple sensors (e.g., 1 emitter and 5 sensors can produce 5 light paths). In yet other examples, multiple channels can be created using different light paths from multiple emitters to multiple sensors (e.g., 2 emitters and 2 sensors can produce 4 lights paths including 2paths from a first emitter to each of the 2 sensors and 2 paths from a second emitter to each of the 2 sensors). The one or more light emitters can produce light in ranges corresponding to infrared (IR), green, amber, blue and/or red light, among other possibilities. In some examples, a light emitter can be a light emitting diode (LED) and a light sensor can be a photodiode.

The accelerometer 106 can provide time domain acceleration output signals indicative of acceleration due to movements of the user. For example, the device 112 can be worn on a user's wrist, and the accelerometer output signals can be indicative of the arm movements (i.e., arm swings) made by the user. In other examples, the accelerometer output signals can be indicative of the gait (i.e., foot strike rate) of the user. In some examples, the accelerometer can be a three-axis accelerometer providing three-dimensional acceleration outputs (e.g., 3 channels of acceleration outputs).

In operation, the light emitter 102 can transmit a light beam to the user's skin 114, and the light beam can be reflected by the user's skin 114 and received by the light sensor 104. The light sensor 104 can convert this light into an electrical signal indicative of the intensity thereof. This electrical signal can be in analog form and can be converted into digital form by ADC 105b. The digital signal from the ADC 105b can be a time domain PPG heart rate signal which can be fed to the processor 108. The outputs of the accelerometer 106 can also be converted to digital form using ADC 105a. The processor 108 can receive the digitized PPG signal from the light sensor 104 and the digitized accelerometer output signals from the accelerometer 106, and can process these signals to provide a heart rate (HR) output signal to the I/O unit 110. The I/O unit 110 can take the form of one or more of a storage device, a visual display, an audible annunciator, a touch screen integrated with device 112, or other output indicator. The I/O unit 110 can, under program control from the processor 108, provide historical information in visual (numeric, tabular, graphic) or audible (synthesized voice or tone) form of the detected heart rate over a period of time. As one non-limiting example, a visual graph can be displayed showing the HR calculated for each 5 minutes during a prior fixed time interval (e.g., 1 hour) or after an exercise period has been completed as determined by an indication thereof from the user. The I/O unit 110 can also provide, under control of the processor 108, average heart rate information or statistical information of the heat rate over a prior time period or periods. As a further example, the I/O unit 110 can provide current heart rate values as "real time" or instantaneous heart rate values displayed to the user periodically (e.g., every second) during the course of an ongoing exercise program.

The I/O unit 110 can be coupled to one or more of remote unit 118, touch screen 120 and microphone/speaker 122 via wired or wireless communication links 124. The remote unit 118 can be a smart phone or other I/O device conveniently carried or worn by the user, or can be a distant computer or data server such as the user's home computer or the user's cloud storage service. The I/O unit 110 can receive input from the remote unit 118 or can receive input from the user by means of the touch screen 120 and/or the microphone/speaker 122.

Figure 2:
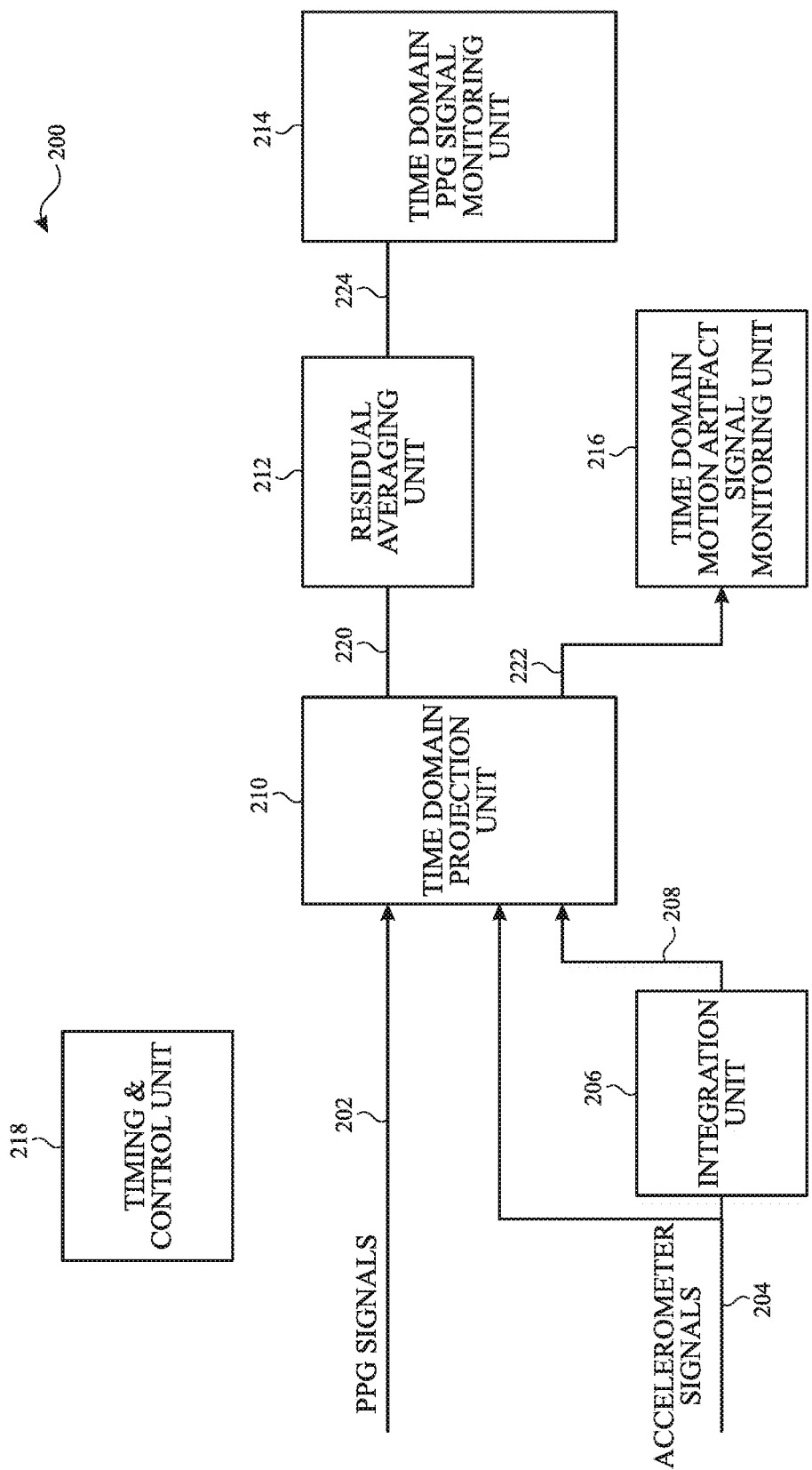
FIG. 2 illustrates an exemplary block diagram of functional units that can be contained within or controlled by a processor according to examples of the disclosure.

FIG. 2 illustrates an exemplary block diagram of functional units that can be contained within or controlled by the processor 108 of FIG. 1. The functional units can be implemented as discrete hardware units such as, for example, digital signal processors (DSP), application specific integrated circuits (AISC), field programmable logic arrays (FPGA), or the like. The functional units can be combined into one or more interconnected devices. Alternatively, the functional units can be implemented in the form of software or firmware configured to operate a programmable processor. Further, the functional units can be a combination of discrete hardware, software and firmware.

As illustrated in FIG. 2, the block diagram can include an integration unit 206, time domain projection (TDP) unit 210, residual averaging unit 212, time domain PPG signal monitoring unit 214, time domain motion artifact signal monitoring unit 216 and timing and control unit 218. The functions of these units are discussed in more detail below.

It should be understood that additional units can be included such as filter units or post-processing units. For example, a filter unit can receive the (raw) PPG signals from ADC 105b sampling the light sensor 104 of FIG. 1, which can operate as a PPG sensor of the device 112. These PPG signals can be time domain signals including components indicative of a user's heart rate and motion artifact components. The filter unit can, for example, be a third order band-pass filter having a band-pass of 0.5-8 Hz corresponding to 30-480 bpm (beats per minute), or any other range of expected heart rate frequencies. The filter unit can remove signals that do not have frequency components that fall within or near the range expected for heart rate monitoring under various expected user conditions or activity levels. The output of the filter can be a filtered PPG signal which can be fed to the TDP unit 210.

Returning to the block diagram illustrated in FIG. 2, time domain PPG signals 202 from the PPG sensor can be sampled periodically by the ADC 105b, such as, for example, at a sampling frequency of 128 Hz. A sampling window can be established to assemble a fixed number of samples. Thus, in some examples, an 8 second sampling window can collect time domain PPG signal 202 data in the form of 128×8=1024 sampling points to feed to the TDP unit 210. In this way, the time domain projection algorithm can be performed using 8 seconds worth of data (e.g., from time t=0 to t=8). Although described here as an eight second sampling window, the sampling window can be selected to be 2-8 seconds in duration in some examples. In other examples the range of sampling windows can be larger, such as from 0.5 seconds to 10 seconds, The time domain projection algorithm can consider overlapping, sliding sampling windows. The spacing between the overlapping windows can be 1-3 seconds in some examples, but the example that follows will assume one second spacing. As new data samples (e.g., the next 128 samples taken in the next one second based on a one second spacing) are taken by the ADC 105b, the first second's worth of data (e.g., 128 samples from time t=0 to t=1) can be discarded or excluded from the sampling window under consideration and the time domain projection algorithm can operate on a new sampling window of 1024 data points including the new data points (e.g., 1024 samples from time t=1 to t=9). The process can be repeated such that the time domain projection algorithm can be applied with respect to each window of 1024 time domain data points (hence the sliding window). Thus, the TDP unit 210 can execute the time domain projection algorithm 8 times (assuming an 8 second window with 1 second spacing) for every second of PPG data (excluding the data at the start and end of operation). The residual output of the TDP unit 210 from overlapping windows can be averaged as described in more detail below with respect to residual averaging unit 212.

Similarly, time domain accelerometer signals 204 from the accelerometer can be sampled periodically by the ADC 105a, for example, at a sampling frequency of 128 Hz. In some examples, the sampling rate of ADC 105a and 105b, can be the same even though the sensors themselves can be operated by different timing sources (e.g., clocks) with an unknown and/or variable time-alignment error (e.g., on the order of hundreds of milliseconds). Overlapping, sliding sampling windows can be established with the same duration and spacing as the PPG signal sampling windows described above. Thus, time domain accelerometer signals 204 can be fed to the TDP unit 210 corresponding to the same sampling window used for time domain PPG signals 202. As discussed above, the accelerometer 106 can be a three-axis accelerometer producing three separate signal streams, each signal stream corresponding to one axis of the accelerometer measurement. Thus, the accelerometer signals can be considered a three-channel signal stream.

The timing and control unit 218 can provide various timing and control signals to the other components of FIG. 2 as needed. For example, the timing and control unit can be used to match sampling windows of the PPG signal and accelerometer signals for implementation of the time domain projection algorithm.

The time domain accelerometer signals 204 can also be received by integration unit 206. The integration unit 206 can integrate the accelerometer signals 204 for each channel independently over time (e.g., cumulative sum). The integrated signals can be mean-centered and variance-scaled to have the same variance as the original accelerometer signals 204. Thus, the mean-centered and scaled output of the integration unit 206 can be integrated accelerometer signals 208 that be fed to the TDP unit 210. Integrated accelerometer signals 208 can be used to identify time-delayed correlations between the PPG signal stream and the accelerometer signal stream to account for physical or physiological response delays and timing misalignment between the PPG and accelerometer samples. For a three-axis accelerometer, there can be three channels of integrated accelerometer signals 208. In some examples, the accelerometer signals 204 and integrated accelerometer signals 208 can be combined to form a six pseudo-channel sample stream that can be fed to the TDP unit 210. In other examples, the two signal streams can be fed separately into the TDP unit 210. In yet other examples, the integration unit 206 can be a part of TDP unit 210, in which case only accelerometer signals 204 can be fed into the TDP unit 210.

As discussed above, the TDP unit 210 can receive the windowed samples of the time domain PPG signals 202, accelerometer signals 204 and integrated accelerometer signals 208. The PPG signals 202 can contain both the desired heart rate signals and the undesired disturbance signal (i.e., the motion artifact). The time domain projection algorithm implemented in TDP unit 210 can isolate the desired heart rate signals in the PPG signal stream by identifying the best representation of the accelerometer signals (including the integrated accelerometer signals) in the PPG signal stream and then removing that representation of the accelerometer signal from the PPG signal stream. The remaining residual signal can be representative of the heart rate of the user after removing any motion artifacts. The time domain projection algorithm is described in more detail below.

The time domain projection algorithm outputs an estimate of the time domain PPG signal stream with the motion artifact removed, referred to as the residual signals 220, corresponding to the window of the input signals. The residual averaging unit 212 can receive the residual signals 220 for multiple overlapping windows and can average the residual signals 220 to construct a final time domain series for the PPG signal 224. The final time domain series for the PPG signal 224 can be received by the time domain PPG signal monitoring unit 214. The time domain PPG signal monitoring unit 214 can use time domain algorithms to extract instantaneous heart rate or heart rate variability via peak-to-peak interval measurements, for example, although other techniques can be used. The time domain PPG signal monitoring unit 214 can also use time domain algorithms to measure average heart rate. Residual averaging and heart rate monitoring algorithms are described in more detail below.

Additionally, in some examples, the TDP unit 210 can output the extracted motion artifact signals 222. The motion artifact signals can be received by the time domain motion artifact monitoring unit 216. The motion artifact monitoring unit 216 can use motion artifact signals 222, for example, to detect motion sensitivity and thereby determine the fidelity of the connection between the device 112 and the user's skin. Thus, in some examples, the motion artifact can be used to notify a user to properly secure the device 112 to the skin (e.g., by tightening a band). In other examples, the motion artifact can be used to determine which algorithms to apply for processing the PPG signal (e.g., different algorithms or compensation can be applied for a poor connection between the PPG sensor and the skin). In other examples, motion artifact signals 222 can be discard or ignored.

Figure 3:
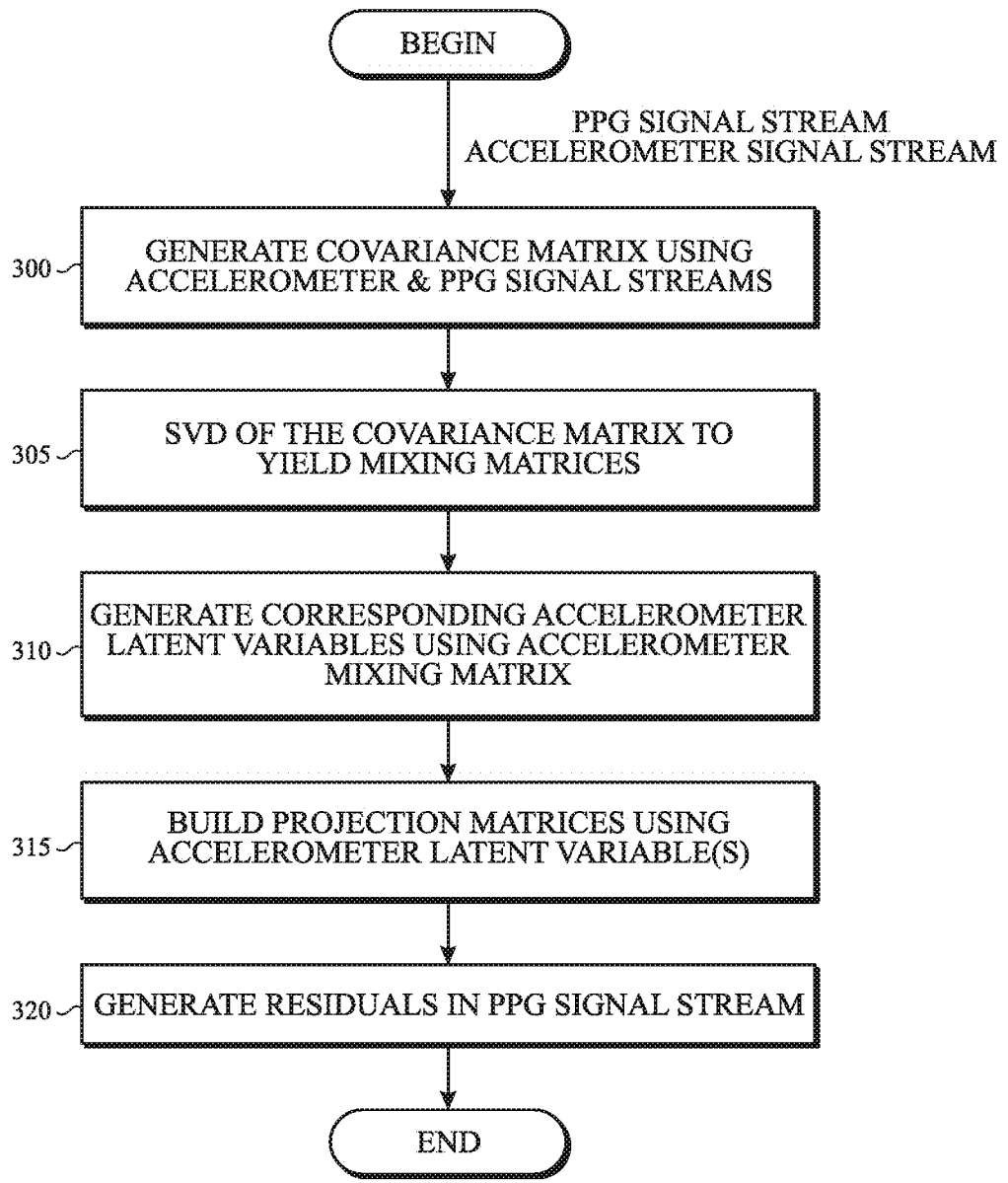
FIG. 3 illustrates an exemplary time domain projection algorithm for removing motion artifacts according to examples of the disclosure.

In general, the time domain projection algorithm can use a least squares fit in order to identify the best representation of the accelerometer signal stream within the PPG signal stream. For example, the algorithm can use ordinary least squares (OLS) or partial least squares (PLS) regression techniques to identify the motion artifact contribution of the PPG signal stream attributable to the acceleration signal stream. FIG. 3 illustrates an exemplary time domain projection algorithm for removing motion artifacts according to examples of the disclosure. The PPG signal stream and accelerometer signal stream can be used to determine a covariance between the two signal streams by generating a covariance matrix, for example (300). In an example with a three-axis accelerometer and a single PPG sensor, the PPG signal stream can be represented by a vector (e.g., a 1×N vector, where N can be the number of samples in the sampling window) and the six pseudo-channel accelerometer signal stream can be represented by a matrix (e.g., a 6×N matrix). The covariance matrix can be generated by taking the matrix product of the accelerometer signal stream and the PPG signal stream. Mathematically, this can be represented as shown in equation (1):

$$\mathrm{Cov} = A_{data} \cdot P_{data}^{T} \qquad (1)$$

where Cov can represent the covariance matrix, $A_{data}$ can represent the accelerometer signal stream and $P_{data}$ can represent the PPG signal stream.

A singular value decomposition (SVD) can be used to factor the covariance matrix to yield mixing matrices that can be used to generate latent variables (305). The SVD of the covariance matrix can be expressed mathematically as shown in equation (2):

$$Cov = WDQ^T \qquad (2)$$

where Cov can represent the covariance matrix, W can represent the accelerometer mixing matrix, D can represent a diagonal matrix and $Q^T$ can represent the PPG mixing matrix. The diagonal matrix can be used to explain the covariance (and therefore correlation) of each acceleration latent variable in the new basis, but in some examples the diagonal matrix can be ignored because the latent variables are already ordered according to the degree of correlation. Furthermore, in the case of a single PPG signal stream, the diagonal matrix only contains one entry and can be ignored. Additionally, in the case of a single PPG signal stream, mixing matrix $Q^T$ can be a 1×1 unity matrix. In a case with multiple PPG signal streams (i.e. multivariate PPG signals stream), however, $Q^T$ can have larger dimensions and be non-unity. Mixing matrix W, output by the SVD operation, can be an expression of how to generate the best linear combination of accelerometer signals corresponding to the motion artifact in the PPG signal stream.

The mixing matrices can be used to generate latent variables for the accelerometer signal stream and PPG signal stream (310). Accelerometer latent variables can be generated using the accelerometer mixing matrix (i.e. transforming the accelerometer data from the original basis to a new covariance maximizing basis), and PPG latent variables can be generated using the PPG mixing matrix. Mathematically, the generation of latent variables can be expressed as shown in equations (3) and (4):

$$T = A_{data}^T \cdot W \qquad (3)$$

$$U = P_{data}^T \cdot Q \qquad (4)$$

where T can represent the accelerometer latent variables (i.e., an expression of the accelerometer signal stream in the latent variable space), $A^T_{data}$ can represent the transpose of the accelerometer signal stream, W can represent the accelerometer mixing matrix, U can represent the PPG latent variable(s), $P^T_{data}$ can represent the transpose of the PPG signal stream (i.e., an expression of the PPG signal stream in the latent variable space), and Q can be the transpose of PPG mixing matrix $Q^T$. As discussed above, in the case of a single PPG signal stream, the mixing matrix $Q^T$ can be unity and therefore U can be simply the transpose of the PPG signal stream. The latent variables can be used for least squares fitting techniques to separate the motion artifact and residual heart rate signal from the original PPG signal.

The latent variables can be used to build least-squares projection matrices (315). In some examples, only a single latent variable can be projected, but in other examples, multiple or all latent variables can be projected. A projection matrix can be generated from some or all of the latent variables. The projection matrix can be represented in the latent variable space. The residual projection matrix represented in the latent variable space can be generated by subtracting the projected matrix from an identity matrix. The generation of these matrices can be expressed as shown in equations (5) and (6):

$$P = X \cdot (X^T \cdot X)^{-1} \cdot X^T \qquad (5)$$

$$R = I - P \qquad (6)$$

where P can represent the projection matrix projected represented in the latent variable space, X can represent the portion of latent variable matrix T used to generate the projection matrix, R can represent the residual projection matrix, and I can represent an identity matrix. In an example with only a single latent variable projected, X can be the first column vector of T. In an example projecting $N_{pc}$ latent variables, X can be formed of the first $N_{pc}$ columns vectors of T, where $N_{pc}$ can represent the number of components projected.

The residuals can be generated for the PPG signal stream by projecting the residual matrix and un-mixing the residuals (320). The residual portion can be used to determine the heart rate. Mathematically, the projection and un-mixing of residuals can be expressed as shown in equation (7):

$$A = (R \cdot U) \cdot Q^T \qquad (7)$$

where A can be the residual portion of the PPG signal stream after removing the motion artifact, R can represent the residual projection matrix, U can represent the PPG latent variables and $Q^T$ can represent the PPG mixing matrix.

The above description of the time domain projection algorithm generally follows the PLS algorithm. If all latent variable components are used (e.g., 6 components corresponding to 6 pseudo-channels), an OLS algorithm can be used instead. The OLS algorithm can use the accelerometer signal stream to generate the projection and residual matrices, and generate the PPG residual signals. The OLS algorithm can be expressed mathematically as shown in equations (8)-(10):

$$P = X \cdot (X^T \cdot X)^{-1} \qquad (8)$$

$$R = I - P \qquad (9)$$

$$A = R \cdot R \cdot P_{data}^T \qquad (10)$$

where P can represent the projection matrix projected into the latent variable space, X can represent the accelerometer signal stream $A_{data}^T$, R can represent the residual matrix formed using the projection matrix of equation (8), I can represent an identity matrix, A can represent the residual portion of the PPG signal stream after removing the motion artifact and $P^T_{data}$ can represent the original PPG signal stream.

Figure 4:
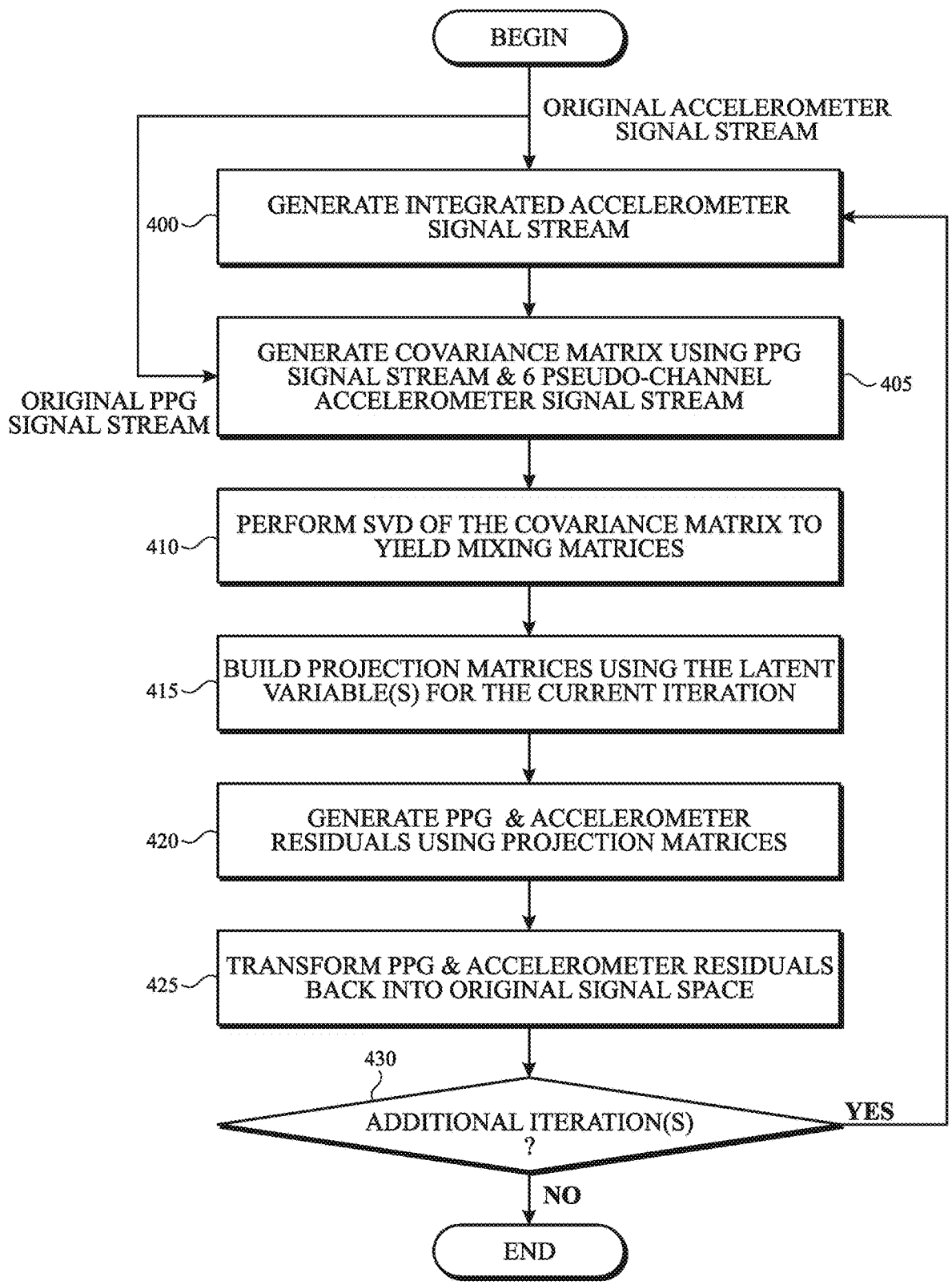
FIG. 4 illustrates an exemplary iterative time domain projection algorithm for removing motion artifacts according to examples of the disclosure.

The time domain projection algorithm illustrated in FIG. 3 performs one least squares fitting of some or all of the accelerator latent variables to the PPG signal stream in order to remove motion artifacts from the PPG signal stream. One least squares fitting can reduce the amount of noise introduced into the output PPG signal stream as each least squares fitting can provide an opportunity to add noise to the PPG signal stream. In other examples, an iterative time domain projection algorithm can be used. The iterative process can provide more opportunities to introduce noise, but projecting single latent variables independently can provide a higher fidelity fitting and not all latent variables have much impact in removing the motion artifact. FIG. 4 illustrates an exemplary iterative time domain projection algorithm for removing motion artifacts according to examples of the disclosure.

In the time domain projection algorithm of FIG. 4, in the first iteration, the original accelerometer signal stream can be used to generate an integrated accelerometer signal stream (400). The integrated accelerometer signal stream can be generated as described above such that the integrated signal stream is mean-centered and has the same variance as the accelerometer signal stream. In subsequent iterations, the deflated accelerometer signal streams (i.e., the accelerometer streams residual projection and transformation back into the original space as in equation (15), for example) from previous iterations can be used to regenerate the integrated accelerometer signal stream, as described in more detail below. The PPG signal stream and the accelerometer signal stream including the integrated accelerometer signals can be used to determine a covariance between the two signal streams by generating a covariance matrix (405). In the first iteration, the original PPG signal stream can be used to generate the covariance matrix, but in subsequent iterations, the residual PPG signal stream from the previous iteration can be used, as described in more detail below. Generically, the generation of the covariance matrix can be expressed as: Cov=A·$P^T$, where Cov can represent the covariance matrix, A can represent the original or deflated accelerometer signal stream, and P can represent the original or residual PPG signal stream.

A singular value decomposition (SVD) can be used to factor the covariance matrix to yield mixing matrices that can be used to generate latent variables (410). The mixing matrices can be used to generate latent variables for the accelerometer signal stream and PPG signal stream (415). The mixing matrices can be respectively expressed as: T=$A^T$·W; U=$P^T$·Q, where T can represent the accelerometer latent variables, $A^T$ can represent the transpose of the accelerometer signal stream, W can represent the accelerometer mixing matrix, U can represent the PPG latent variables, $P^T$ can represent the transpose of the PPG signal stream, and Q can be the transpose of PPG mixing matrix $Q^T$. As, discussed above, in examples using a single PPG sensor, the mixing matrix $Q^T$ can be unity.

The latent variables can be used to build projection matrices (415). In some examples, only a single latent variable can be projected in an iteration, but in other examples, more than one latent variable can be projected in an iteration. A projection matrix can be generated from the accelerator latent variables projected during the iteration. The residual projection matrix can be generated by subtracting the projection matrix from an identity matrix. The residual projection matrix can be used to generate PPG and accelerometer residuals (420). The PPG and accelerometer residuals can be transformed back into the original signal space by un-mixing the residuals (425). The residuals transformed back into the original signal space can be expressed mathematically as:

$$P=((R·U)·Q^T)^T \quad (14)$$

$$A=((R·T)·W^T)^T \quad (15)$$

where P can represent the residual signal stream transformed back into the original space, A can represent the residual acceleration signal stream transformed back into the original space, R can represent the residual projection matrix, U and T can represent the latent variable matrices, and W and $Q^T$ can represent the mixing matrices.

The unmixed PPG and accelerometer residuals can be used at 400 for subsequent iterations. The algorithm can determine whether additional iterations can be performed and, if desired, the additional iterations can be executed (430). If no additional iterations can be performed or additional iterations are undesired, the algorithm can end. In some examples, the number of iterations can be preset. In other examples, the number of iterations can be determined dynamically based on various conditions. For example, the iterations can continue or be terminated based on the degree of correlation between latent variables and the PPG signal (e.g., a high correlation can correspond to a significant motion artifact to remove).

It should be noted that although the PPG and accelerometer sensors can generate values with arbitrary scaling, the absolute magnitude of each signal stream need not be known and the time domain projection algorithm can operate without making any assumption of the absolute magnitude of the inputs. Instead, the time domain projection algorithm can assume the motion artifact generated in the PPG signal can be represented in the accelerometer signals and the SVD can determine the portion of the PPG signal most correlated with accelerometer signals. That correlated portion of the PPG signal can be removed from the PPG signal as the motion artifact. The heart rate portion of the PPG signal can be uncorrelated or have a poor correlation with the accelerometer signal over the sampling window and therefore the heart rate portion of the PPG signal can remain unremoved.

Figure 5A:
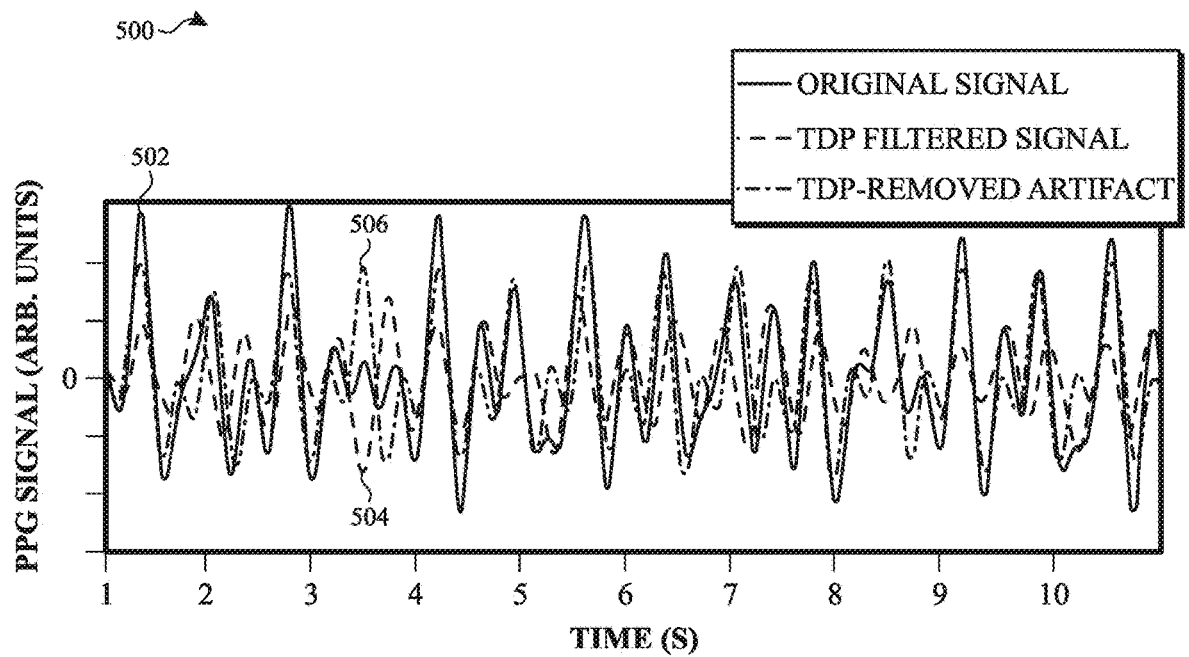
FIGS. 5A through 5N show plots illustrating the operation of the time domain projection algorithm according to examples of the disclosure.
Figure 5B:
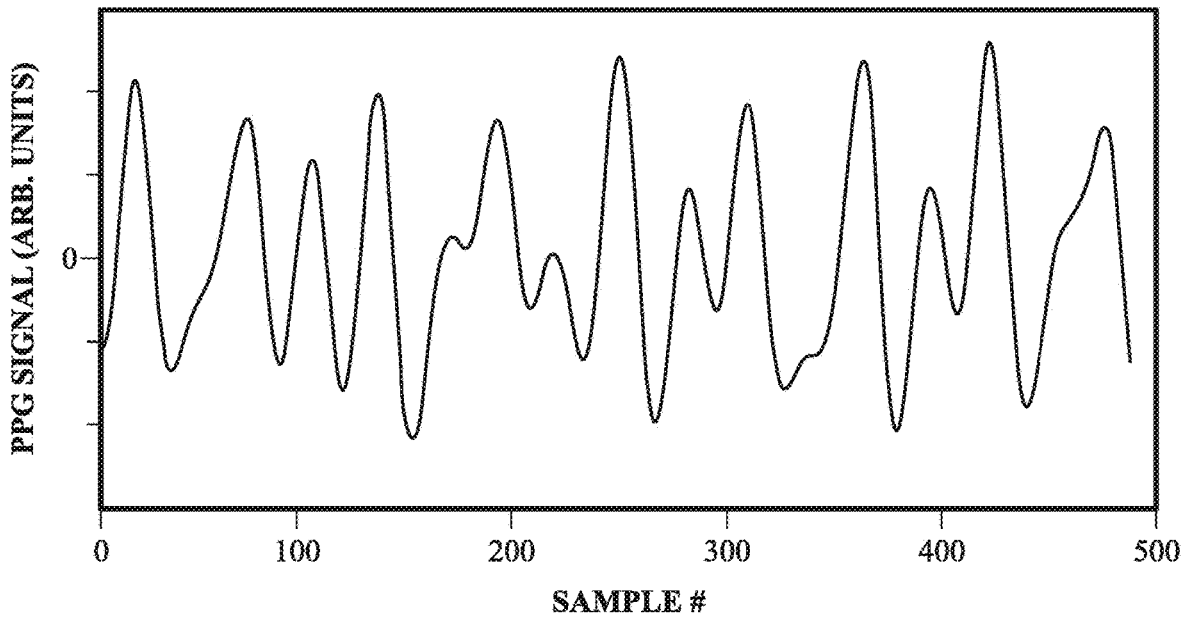
Figure 5C:
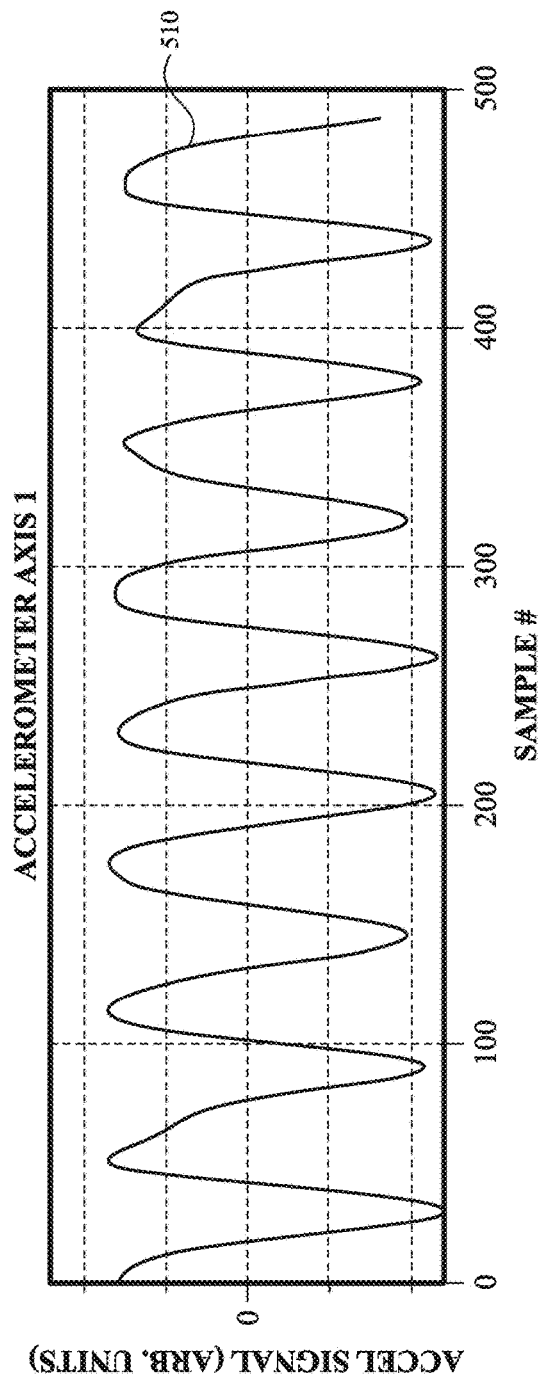
Figure 5D:
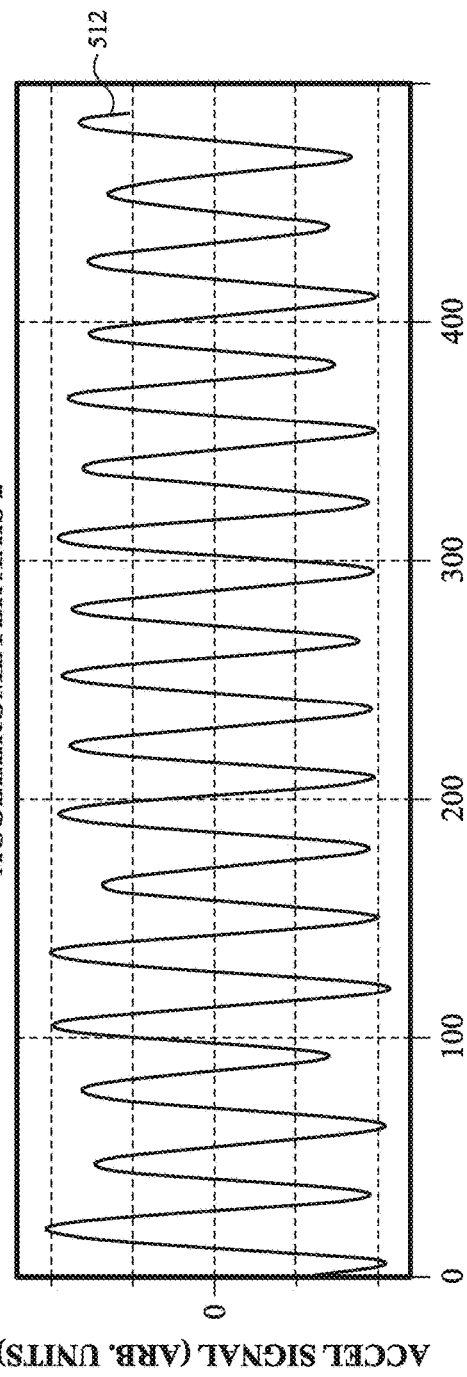
Figure 5G:
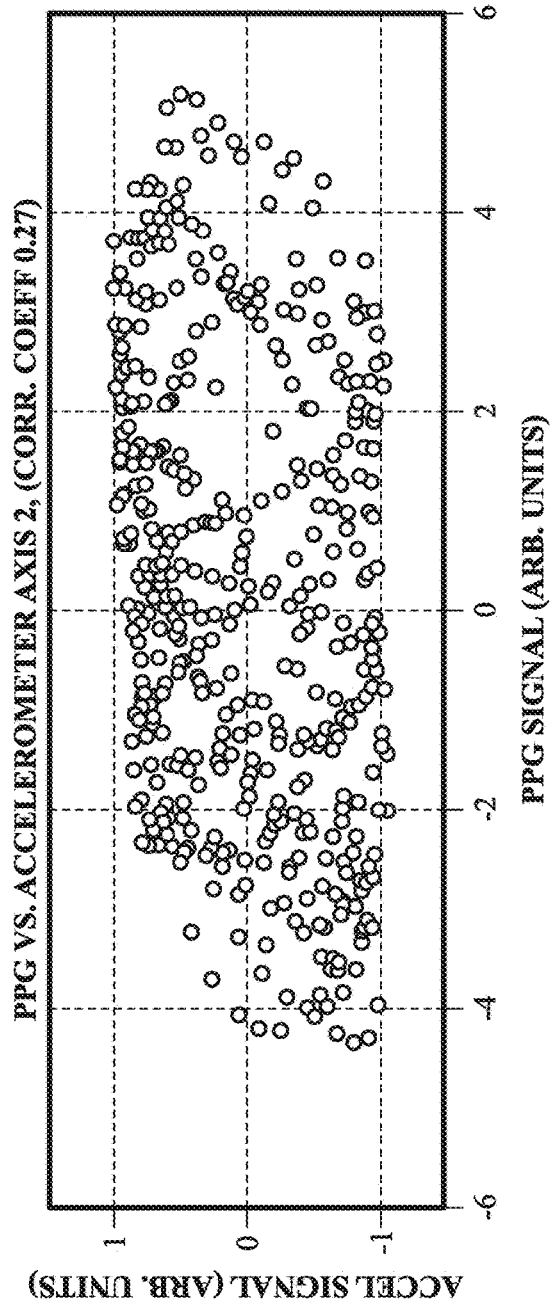
Figure 5H:
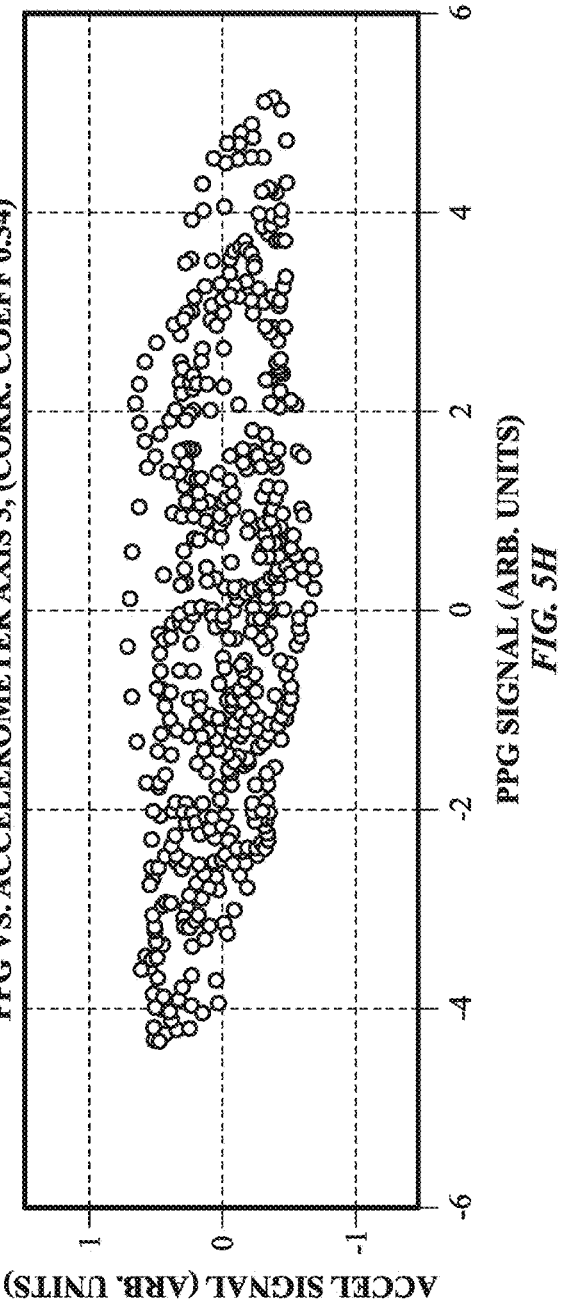
Figure 5I:
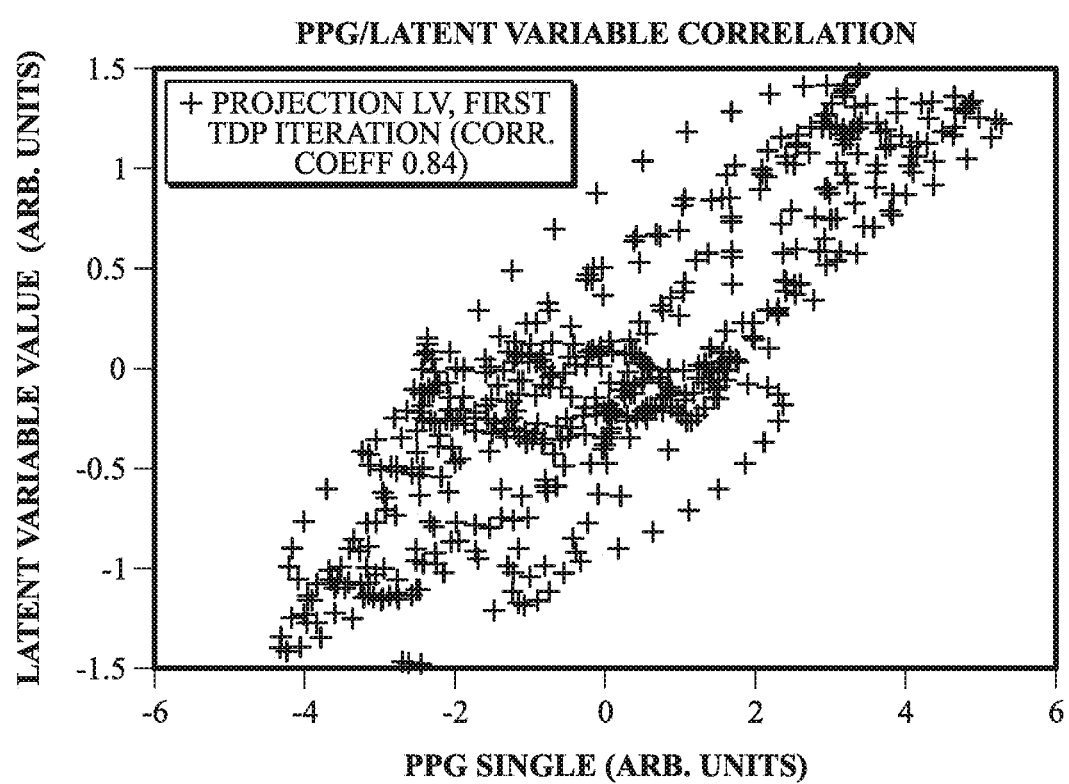
Figure 5J:
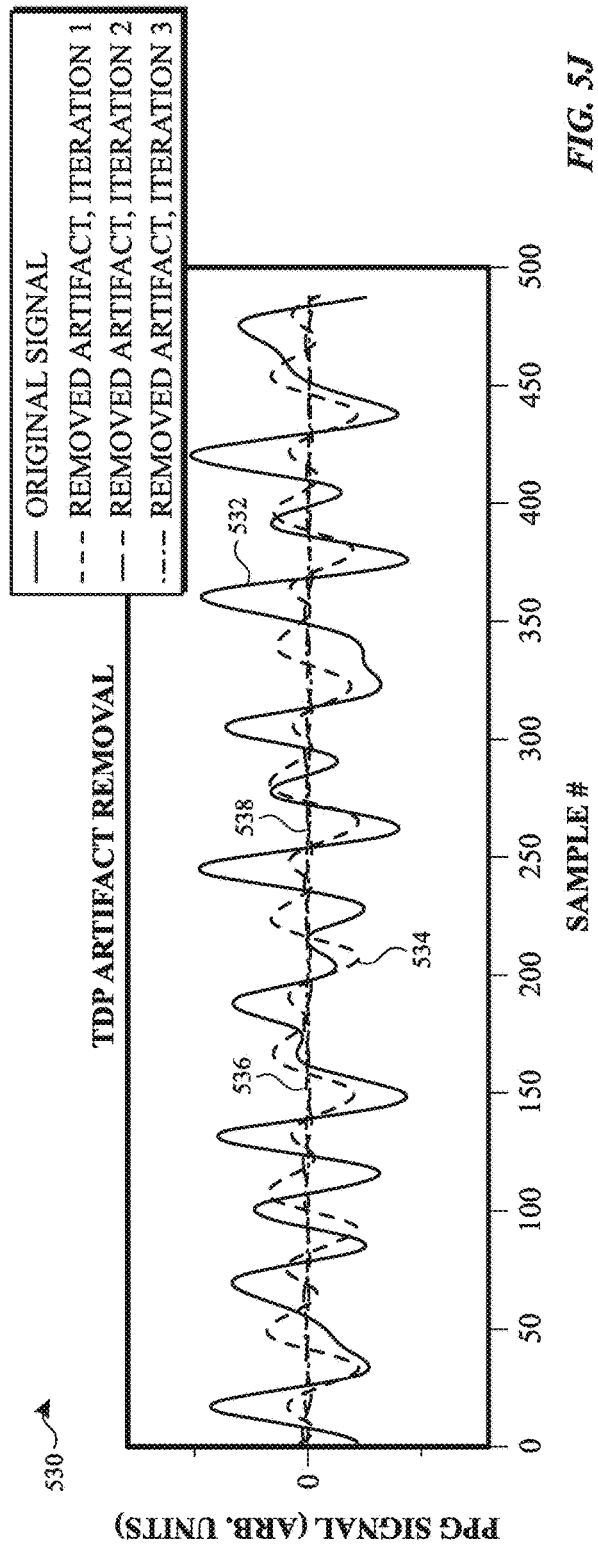
Figure 5K:
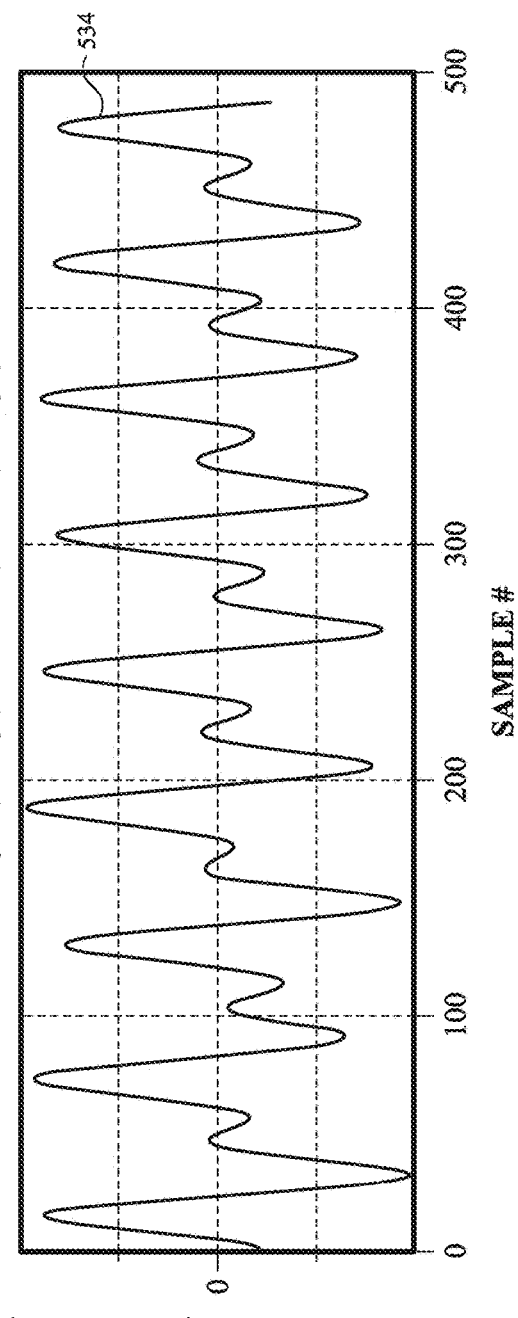
Figure 5L:
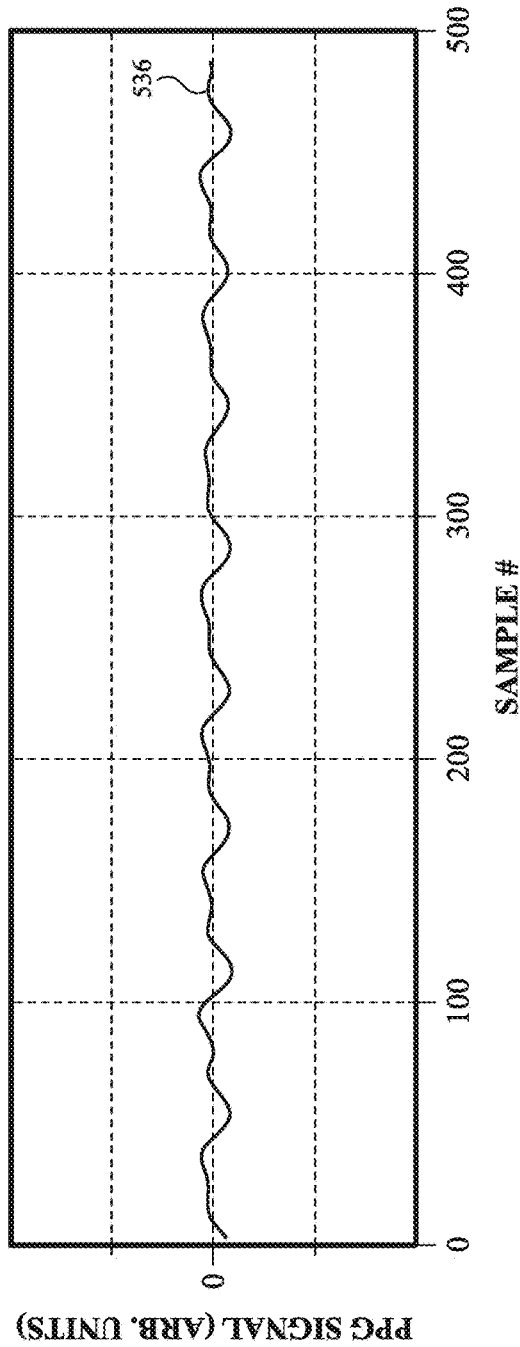
Figure 5M:
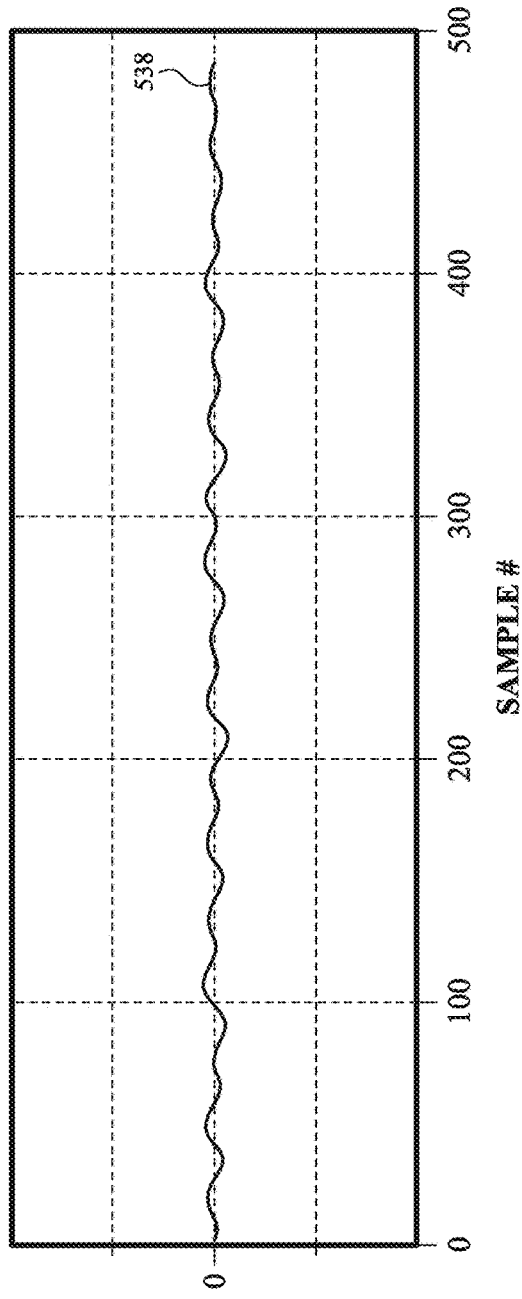
Figure 5N:
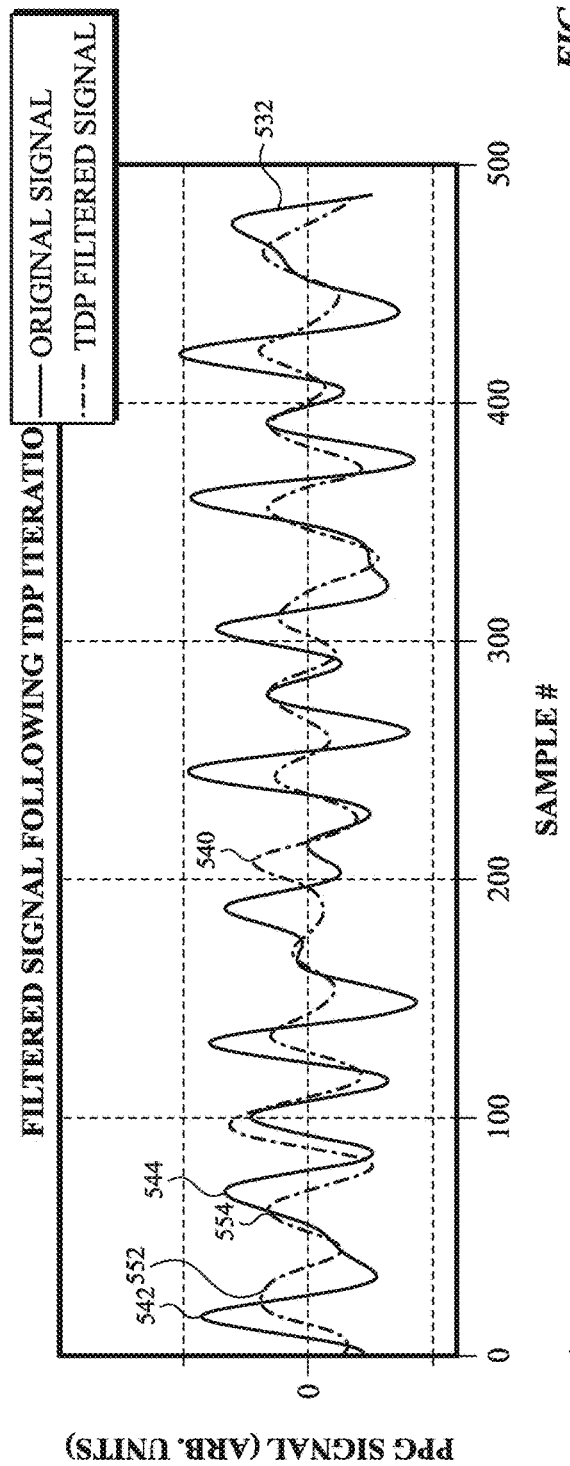

FIGS. 5A through 5N show plots illustrating the operation of the time domain projection algorithm according to examples of the disclosure.

FIG. 5A illustrates an exemplary plot 500 of the time domain projection algorithm on the PPG signal according to examples of the disclosure. Curve 502 illustrates the original time domain signal received from the PPG sensor. Curve 502 can correspond to time domain PPG signal 202 input into TDP unit 210. As discussed above with respect to time domain PPG signal 202, curve 502 can include a heart rate signal as well as a disturbance signal caused by motion, for example. Curves 504 and 506 can illustrate the outputs of the time domain projection algorithm. For example, curve 504 can correspond to the residual PPG signal 220 and can represent the output heart rate. Curve 506 can correspond to the motion artifact signals 222 output from the TDP unit 210 and can represent the disturbance to be removed from the original PPG signal. Thus, the time domain projection algorithm can accept the original PPG signal 502 as an input, perform the time domain projection algorithm (e.g., 4 iterations of PLS projecting 1 component per iteration), and output a filtered PPG signal 504 which removes the motion artifact signal 506. It should be noted that the removed motion artifact signal 506 can generally follow the peaks of the original PPG signal 502. In contrast, removing the motion artifact signal 506 can illustrate that the true heart rate signal of curve 504 often has peaks that are not aligned in the time domain with original PPG signal 502. These peaks of curve 504 can be used to extract the true heart rate as will be discussed in more detail below.

FIGS. 5B through 5E illustrate plots of exemplary input signals received from PPG and accelerometer sensors according to examples of the disclosure. Specifically, FIG. 5B illustrates a plot of an original PPG signal 508 recorded by a PPG sensor. FIG. 5C through 5E illustrate plots of exemplary accelerometer signals 510, 512 and 514 from respective axes of a three-axis accelerometer. Signals 508, 510, 512 and 514 can be sampled during the same time period (e.g., samples 0-500) assuming the sensors have the same sampling rate. As discussed above, although the sensor data can correspond to the same time period, the correlation between the PPG signal and the accelerometer signal can be delayed to due to physical and physiological response delays and time misalignment between the samples.

The correlation between accelerometer signals from any individual axis of the accelerometer and the PPG signal can be poor. FIGS. 5F, 5G and 5H, for example, can illustrate the correlation between the respective accelerometer signals 510, 512 and 514 and the original PPG signal 508. As illustrated in FIG. 5F, the correlation coefficient between accelerometer signals 510 (i.e., accelerometer axis 1) and the PPG signals can be 0.38. As illustrated in FIG. 5G, the correlation coefficient between accelerometer signals 512 (i.e., accelerometer axis 2) and the PPG signals can be 0.27. As illustrated in FIG. 5H, the correlation coefficient between accelerometer signals 514 (i.e., accelerometer axis 3) and the PPG signals can be −0.34. A poor correlation between the accelerometer data can make it difficult to remove a motion artifact from original PPG signal 508.

Rather than look at individual correlations between the accelerometer signals 510, 512 and 514 (or the mean-centered, variance-scaled integrated accelerometer signals), the time domain projection algorithm projects a latent variable (i.e., representing a linear combination of the accelerometer signals) such that the covariance between the accelerometer latent variable and the PPG signal can be maximized. The latent variable maximizing the covariance/correlation can be the best representation of the motion artifact in the PPG signal. FIG. 5I illustrates a correlation between an exemplary covariance maximizing accelerometer latent variable and a PPG signal according to examples of the disclosure. As illustrated in FIG. 5I, the correlation coefficient between accelerometer latent variable signals and the PPG signals can be 0.84. The high correlation between the accelerometer latent variable signals and the PPG signals can indicate that the latent variable projection can be a good representation of the acceleration motion artifact in the original PPG signal.

As discussed above, the time domain projection algorithm can be performed once, or iteratively. FIG. 5J illustrates exemplary plot 530 of motion artifact signals removed from an original PPG signal according to examples of the disclosure. For example, curve 532 illustrates an original PPG signal and curves 534, 536 and 538 illustrate motion artifacts removed from the original PPG signal during respective iterations of the time domain projection algorithm. It should be noted that the motion artifact removed during the first iteration (i.e., curve 534), can have a considerably larger amplitude than the motion artifacts removed during the second and third iterations (i.e., curves 536 and 538). The relative size of the first motion artifact can illustrate how effective a first projection of the accelerometer signal can be at removing motion artifacts from the original PPG signal. The relative sizes of the removed motion artifacts can be illustrated in FIGS. 5K through 5M. FIGS. 5K through 5M illustrate plots of exemplary motion artifact signals respectively removed from the original PPG signal according to examples of the disclosure. Curve 534 illustrated in FIG. 5K can corresponding to the motion artifact removed during the first iteration. Curve 534 can be relatively larger than the motion artifacts 536 and 538, illustrated in FIGS. 5L and 5M respectively, that can be removed in the subsequent iterations.

5N illustrates a plot of an exemplary PPG signal after removing a motion artifact signals according to the examples of the disclosure. As in FIG. 5J, curve 532 can represent the original PPG signal. Curve 540 can represent the filtered PPG signal after removing the motion artifact during a first iteration (i.e., curve 534) from the original PPG signal. The filtered PPG signal after removing the motion artifacts during the second and third iterations are not shown as the bulk of the motion artifact can be removed during the first iteration. It should be noted that the peaks of the filtered PPG signal can occur at different times than the original signal. For example, the peak 552 in the filtered PPG signal occurs later in time than peak 542 in the original PPG signal. The subsequent peak 554 in the filtered PPG signal occurs earlier in time than peak 544 in the original PPG signal. The different separation between the peaks can indicate a different heart rate (beats per minute) in the filtered PPG signal than indicated by the separation between peaks in the original PPG signal.

As discussed above, the accelerometer signals 204 from the accelerometer can be integrated in integration unit 206 in some examples (or in TDP unit 210 in other examples). Integrated accelerometer signals 208 can be used to identify time-delayed correlations between the PPG signal stream and the accelerometer signal stream to account for physical or physiological response delays and timing misalignment between the PPG and accelerometer samples. Using all three channels of the accelerometer data and three channels of the integrated accelerometer data can improve artifact removal as illustrated by FIGS. 9A through 9C. FIGS. 9A through 9C illustrate spectrograms of PPG signals before and after removing artifacts according to examples of the disclosure. FIG. 9A illustrates a spectrogram 900 of an original PPG signal. The spectrogram includes the true heart rate signal 902 as well as motion artifact 904 and a first harmonic 906 of motion artifact 904. The motion artifact 904 and first harmonic 906 can make it difficult to identify the true heart rate 902 in the PPG signal. FIG. 9B illustrates a spectrogram 910 of the PPG signal after removing the motion artifact using only three channels of accelerometer signals for the time domain projection algorithm. As illustrated in FIG. 9B, portions of the motion artifact and first harmonic can be removed from the PPG signal as shown by the gaps between motion artifacts 914 and first harmonics 916 of the motion artifact. However, portions of the original motion artifacts (motion artifact 914 and first harmonic 916) can remain along with the true heart rate signal 912. Thus, although the time domain projection algorithm can remove portions of the motion artifact, relying on only three channels can be insufficient to isolate the true heart rate signal within the PPG signal. In contrast, FIG. 9C illustrates a spectrogram 930 of the PPG signal after removing the motion artifact using the accelerometer and integrated accelerometer signals (e.g., 6 pseudo-channels) for the time domain projection algorithm. As illustrated in FIG. 9C, motion artifacts (including harmonics) can be removed and true heart rate signal 922 can remain. Thus, using both accelerometer and integrated accelerometer data in the time domain projection algorithm can provide improved performance for removing motion artifacts.

It should be noted that although FIGS. 9A through 9C show spectrograms (i.e. frequency domain representations), the operation of the time domain projection algorithm can be purely in the time domain.

Figure 6:
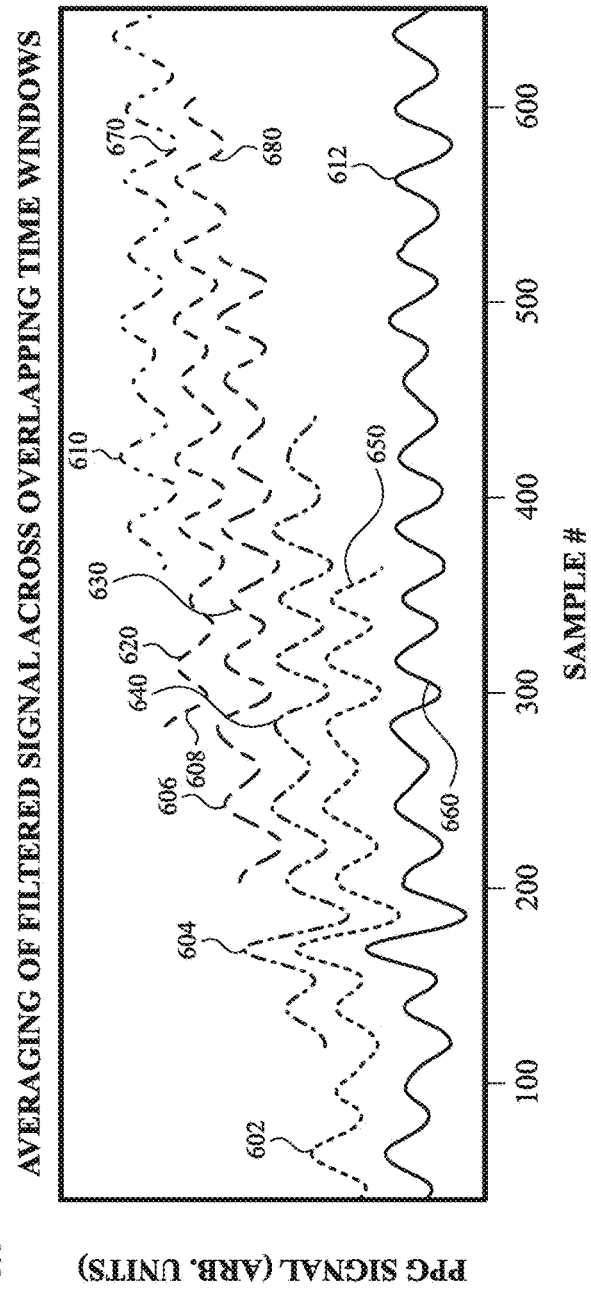
FIG. 6 illustrates an averaging of residual PPG signals from overlapping time intervals to produce a final time domain series for the PPG signal according to examples of the disclosure.

As discussed above, the output of the TDP unit 210 can be the residual PPG signals remaining after removing motion artifacts using the time domain projection algorithm. Each output from the TDP unit 210 contains residual PPG signals (and motion artifact signals) corresponding to a window of interest. In order to construct a final time domain series for the PPG signal, the output residual PPG signals corresponding to overlapping windows can be averaged. FIG. 6 illustrates an averaging of residual PPG signals from overlapping time intervals to produce a final time domain series for the PPG signal according to examples of the disclosure. Plot 600 illustrates five residual PPG signals 602, 604, 606, 608 and 610. The residual PPG signals of the example illustrated in FIG. 6 can have a 4 second sampling window with a 3 second overlap (i.e., 1 second spacing). Thus, except for the end points of the PPG signal input, there can be 4 signal measurements from overlapping windows. For example, peaks 620, 630, 640 and 650 can be averaged to produce peak 660 in the final time domain series for the PPG signal 612 at the output. The same averaging can be performed for any signal value sample at any overlapping time. For example, the measurement 670 of the residual PPG signal from the fifth illustrated window at a given time can be averaged with the corresponding measurement 680 of the residual PPG signal from the fourth illustrated window. Averaging the residual PPG signals from overlapping time windows can reduce noise introduced by the time domain projection algorithm for a higher fidelity PPG signal. Although discussed in terms of averaging overlapping PPG signal measurements, other operations can be performed to generate a composite PPG signal from the residual PPG signal measurements. Additionally, in some examples, fewer than all overlapping PPG signals can be averaged to reduce computational complexity (i.e. averaging 2 or 3 samples rather than all 4 in the example illustrated in FIG. 6.) In other examples, averaging can be selectively performed if the residual PPG signal from the TDP unit 210 contains over a threshold amount of noise which can compromise heart rate detection.

Figure 7:
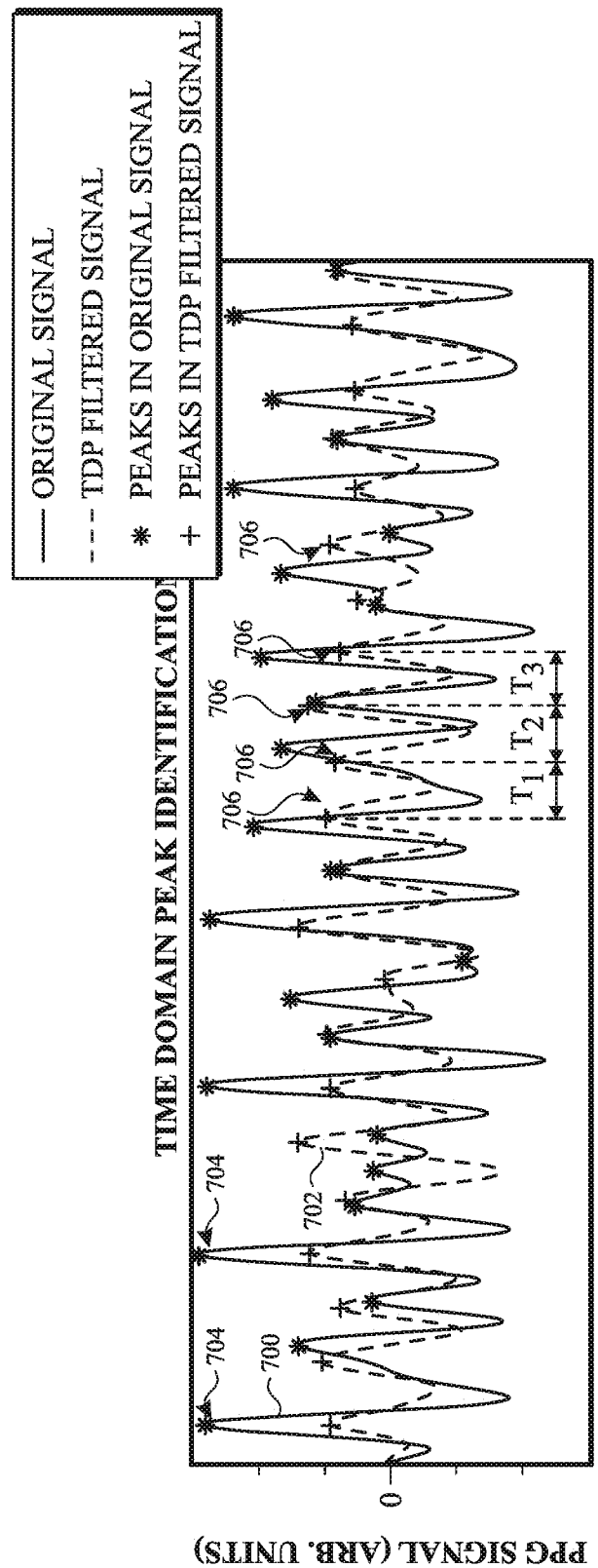
FIG. 7 illustrates time domain techniques for determining heart rate information from a PPG signal according to examples of the disclosure.

As discussed above the, the time domain PPG signal monitoring unit 214 can use various time domain algorithms to extract heart rate information from the final time domain series PPG signal 224. For example, time domain PPG signal monitoring unit 214 can determine instantaneous heart rate or heart rate variability via peak-to-peak interval measurements. FIG. 7 illustrates time domain techniques for determining heart rate information from a PPG signal according to examples of the disclosure. Peaks (i.e., local maxima) can be identified in a PPG signal. For example, as illustrated, in FIG. 7, peaks 704 can be identified in original PPG signal 700 and peaks 706 can be identified in filtered PPG signal 702. The time difference between peaks can be measured. For example, period $T_1$ can be the time difference between two peaks 706 in the filtered PPG signal 702. Similarly, the time difference between subsequent peaks can be measured (e.g., periods $T_2, T_3$, etc.). The instantaneous heart rate can be determined based on the inverse of the corresponding period. For example, $T_1$ can correspond to a time difference of 0.47 seconds and the inverse can 2.12 Hz or 128 bpm. Similarly, $T_2$ can correspond to a time difference of 0.45 second and the inverse can be 2.2 Hz or 133 bpm. Thus, identifying the spacing between adjacent peaks can be used to calculate an instantaneous heart rate from the PPG signal (beat-to-beat heart rate measurement).

The group of instantaneous heart rate measurements can be used to show the variability in heart rate. Heart rate variability can refers to change in heart rate such as changes associated with modes of breathing. For example, heart rate can decelerate when breathing out and heart rate can accelerate when breathing in. In some examples, the variability can be represented as an instantaneous change between consecutive heart rate measurements. For example, the heart rate corresponding to $T_1$ and $T_2$ can be 128 bpm and 133 bpm, and the variability can be expressed as +5 bpm of variability between the two measurements. In other examples, the variability can be expressed in relation to an average heart rate or some other baseline heart rate. For example, the average heart rate can be 132 bpm and the variability corresponding to $T_1$ can be expressed as −4 bpm and the variability corresponding to $T_2$ can be expressed as +1 bpm. It should be understood that variability can be calculated and expressed in other ways.

In other examples, an average heart rate can be determined instead of or in addition to an instantaneous heart rate. The average heart rate can be calculating by measuring the number of peaks in a time window. For example, there can be 22 peaks identified in the 10 second window of the filtered PPG signal 702 corresponding to the estimate heard rate of approximately 132 bpm which can be close to the actual heart rate of the user over the same window. Alternatively, the average heart rate can be calculated by taking an average of the spacing between peaks in a window (e.g., calculated for the instantaneous heart rate) and converting the average spacing into an average heart rate by taking an inverse of the average spacing.

Comparing the peaks 704 and 706 of the original PPG signal 700 and filtered PPG signal 702 shows the benefit of removing the motion artifact from the original PPG signal to identify the peaks associated with heart rate. For example, as shown in FIG. 7, there can be 25 peaks identified in a 10 second window of the original PPG signal 700 corresponding to a gait frequency of approximately 2.67 Hz (160 bpm). In contrast, there can be 22 peaks identified in the 10 second window of the filtered PPG signal 702 corresponding to the estimate heard rate of approximately 132 bpm which can be close to the actual heart rate of the user over the same window. Thus, removing the motion artifact can provide an accurate reading of heart rate, rather than mistakenly reporting a heart rate corresponding to motion artifacts (e.g., foot strike or gait frequencies).

Time domain algorithms for removing a motion artifact from the PPG signal and determining heart rate can provide some advantages over a frequency domain approach. One advantage of processing in the time domain can be no loss in fidelity of the time domain signal. Processing the PPG signal in the frequency domain can result in a loss in fidelity of the time domain signal and can be computationally intensive and require additional hardware. Another advantage of time domain processing over frequency domain processing can be the ability to remove aperiodic motion artifacts (e.g., chaotic motion). In the frequency domain, periodic motion can be identified by distinct peaks at the frequencies of motion. Chaotic motion, in contrast, does not produce distinct peaks, and as a result, these motion artifacts can remain after frequency domain processing. In contrast, the time domain processing described above can remove any motion identified in the accelerometer. The same deficiency of frequency domain processing can make it difficult to detect a less periodic heart rate signal.

Additionally, time domain techniques to extract heart rate provide the ability to detect the instantaneous variability in heart rate in addition to an average heart rate. Frequency domain algorithms can be effective in removing artifacts and determining an average heart rate, but frequency domains can sacrifice time domain information making variability measurements difficult. In contrast, time domain algorithms can preserve timing information and can be used more effectively for measuring instantaneous heart rate and heart rate variability over time.

Figure 8:
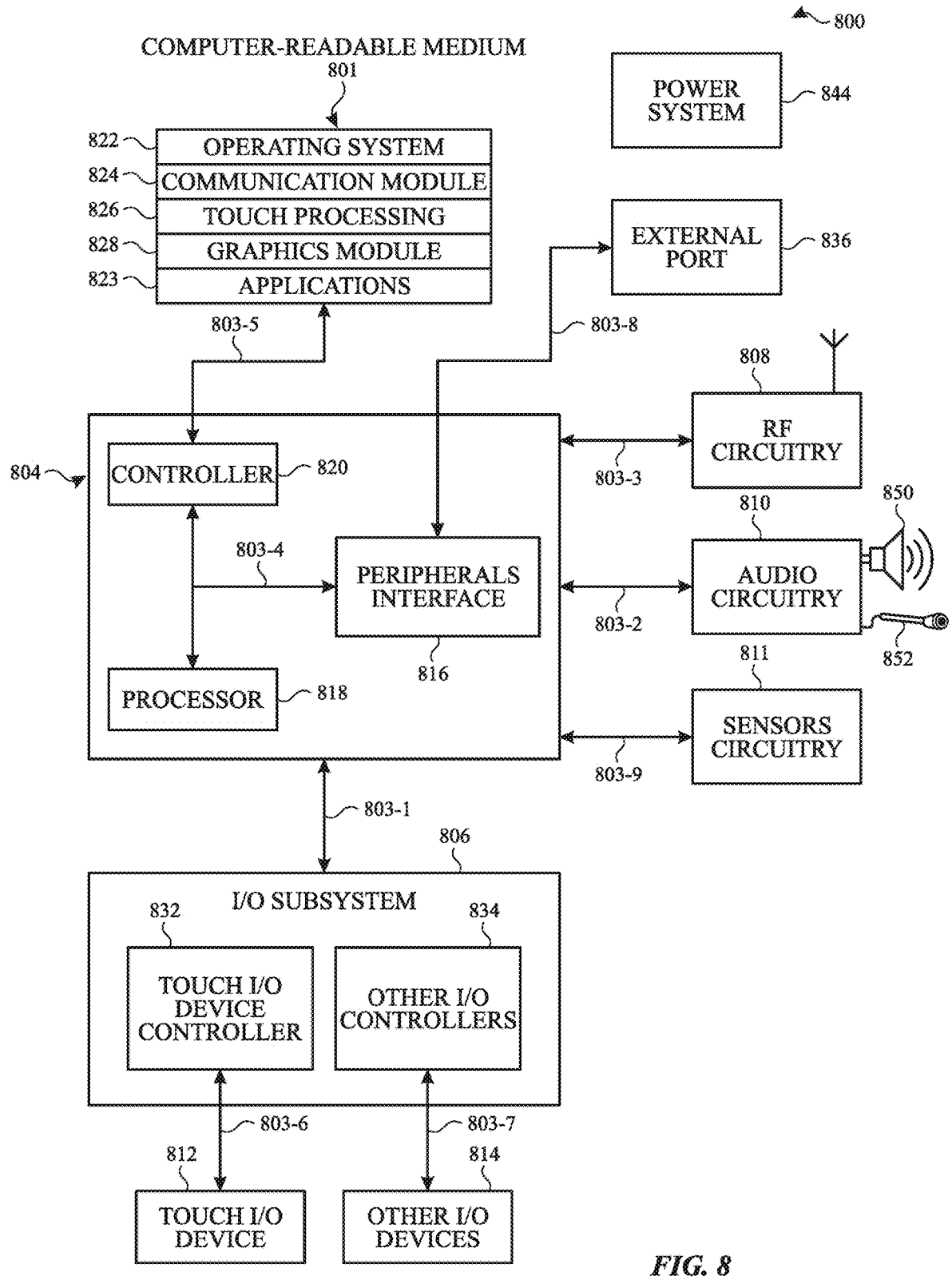
FIG. 8 illustrates a block diagram of an exemplary system architecture that can implement a time domain projection algorithm according to examples of the disclosure.

A system architecture implementing the time domain projection algorithm can be included in any portable or non-portable device including but not limited to a wearable device (e.g., smart band, health band, smart watch), a communication device (e.g., mobile phone, smart phone), a multi-media device (e.g., MP3 player, TV, radio), a portable or handheld computer (e.g., tablet, netbook, laptop), a desktop computer, an All-In-One desktop, a peripheral device, or any other system or device adaptable to the inclusion of system architecture, including combinations of two or more of these types of devices. FIG. 8 illustrates a block diagram of an exemplary system architecture 800 that can implement the time domain projection algorithm according to examples of the disclosure. System architecture 800 can generally include one or more computer-readable media 801, processing system 804, I/O subsystem 806, radio frequency (RF) circuitry 808, audio circuitry 810, and sensors circuitry 811. These components can be coupled by one or more communication buses or signal lines 803.

It should be understood that the exemplary architecture shown in FIG. 8 can have more or fewer components than shown, or a different configuration of components. The various components shown in FIG. 8 can be implemented in hardware, software, firmware or any combination thereof, including one or more signal processing and/or application specific integrated circuits.

RF circuitry 808 can be used to send and receive information over a wireless link or network to one or more other devices and includes well-known circuitry for performing this function. RF circuitry 808 and audio circuitry 810 can be coupled to processing system 804 via peripherals interface 816. Interface 816 can include various known components for establishing and maintaining communication between peripherals and processing system 804. Audio circuitry 810 can be coupled to audio speaker 850 and microphone 852 and can include known circuitry for processing voice signals received from interface 816 to enable a user to communicate in real-time with other users. In some examples, audio circuitry 810 can include a headphone jack (not shown). Sensors circuitry 811 can be coupled to various sensors including, but not limited to, one or more light emitting diodes (LEDs) or other light emitters, one or more photodiodes or other light sensors, one or more photothermal sensors, a magnetometer, an accelerometer, a gyroscope, a barometer, a compass, a proximity sensor, a camera, an ambient light sensor, a thermometer, a GPS sensor, and various system sensors which can sense remaining battery life, power consumption, processor speed, CPU load, and the like.

Peripherals interface 816 can couple the input and output peripherals of the system 800 to one or more processor 818 and one or more computer-readable media 801 via a controller 820. The one or more processors 818 communicate with the one or more computer-readable media 801 via the controller 820. The one more computer-readable media 801 can be any device or medium that can store code and/or data for use by the one or more processors 818. In some examples, medium 801 can be a non-transitory computer-readable storage medium. Medium 801 can include a memory hierarchy, including but not limited to cache, main memory and secondary memory. The memory hierarchy can, as non-limiting examples, be implemented using any combination of RAM (e.g., SRAM, DRAM, DDRAM), ROM, FLASH, magnetic and/or optical storage devices, such as disk drives, magnetic tape, compact disks (CDs) and digital video discs (DVDs). Medium 801 can also include a transmission medium for carrying information-bearing signals indicative of computer instructions or data (with or without a carrier wave upon which the signals are modulated). For example, the transmission medium can include a communications network, including but not limited to the Internet (also referred to as the World Wide Web), intranet(s), Local Area Networks (LANs), Wide Local Area Networks (WLANs), Storage Area Networks (SANs), Metropolitan Area Networks (MAN) and the like.

One or more processors 818 can run various software components stored in medium 801 to perform various functions for system architecture 800. In some examples, the software components can include operating system 822, communication module (or set of instructions) 824, touch processing module (or set of instructions) 826, graphics module (or set of instructions) 828, and one or more applications (or set of instructions) 823. Each of these modules and above noted applications can correspond to a set of instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules can be combined or otherwise re-arranged in various examples. In some examples, medium 801 can store a subset of the modules and data structures identified above. Furthermore, medium 801 can store additional modules and data structures not described above.

Operating system 822 can include various procedures, sets of instructions, software components and/or drivers for controlling and managing general system tasks (e.g., memory management, storage device control, power management, etc.) and facilitates communication between various hardware and software components.

Communication module 824 can facilitate communication with other devices over one or more external ports 836 or via RF circuitry 808 and can include various software components for handling data received from RF circuitry 808 and/or external port 836.

Graphics module 828 can include various known software components for rendering, animating and displaying graphical objects on a display surface. In examples in which touch I/O device 812 is a touch sensing display (e.g., touch screen), graphics module 828 can include components for rendering, displaying, and animating objects on the touch sensing display. The touch I/O device 812 and/or the other I/O device 814 can comprise the I/O unit 110 of FIG. 1, and can also incorporate a UI interface permitting a use to select among programming modes of displaying heart rate data when the I/O device is incorporated into a device 112 of FIG. 1. Further, in relation to FIG. 1, the light emitter 102 and light sensor 104 can be part of the I/O device 814, and the touch screen 120 can correspond to the touch I/O device 812 of FIG. 8. The I/O unit 110 either integrated within device 112 or via coupling to microphone/speaker 122 can also provide audio outputs as part of the user communications corresponding to audio circuitry 810 of FIG. 8. Microphone 852 of FIG. 8 can correspond to the microphone/speaker unit 122 of FIG. 1.

One or more applications 823 can include any applications installed on system 800, including without limitation, a browser, address book, contact list, email, instant messaging, word processing, keyboard emulation, widgets, JAVA-enabled applications, encryption, digital rights management, voice recognition, voice replication, location determination capability (such as that provided by the global positioning system (GPS)), a music player, etc.

Touch processing module 826 can include various software components for performing various tasks associated with touch I/O device 812 including but not limited to receiving and processing touch input received from touch I/O device 812 via touch I/O device controller 832.

I/O subsystem 806 can be coupled to touch I/O device 812 and one or more other I/O devices 814 for controlling or performing various functions. Touch I/O device 812 can communicate with processing system 804 via touch I/O device controller 832, which can include various components for processing user touch input (e.g., scanning hardware). One or more other input controllers 834 can receive/ send electrical signals from/to other I/O devices 814. Other I/O devices 814 can include physical buttons, dials, slider switches, sticks, keyboards, touch pads, additional display screens, or any combination thereof.

If embodied as a touch screen, touch I/O device 812 can display visual output to the user in a GUI. The visual output can include text, graphics, video, and any combination thereof. Some or all of the visual output can correspond to user-interface objects. Touch I/O device 812 can form a touch sensing surface that accepts touch input from the user. Touch I/O device 812 and touch screen controller 832 (along with any associated modules and/or sets of instructions in medium 801) can detect and track touches or near touches (and any movement or release of the touch) on touch I/O device 812 and can convert the detected touch input into interaction with graphical objects, such as one or more user-interface objects. In the case in which device 812 is embodied as a touch screen, the user can directly interact with graphical objects that are displayed on the touch screen. Alternatively, in the case in which device 812 is embodied as a touch device other than a touch screen (e.g., a touch pad), the user can indirectly interact with graphical objects that are displayed on a separate display screen embodied as I/O device 814.

Touch I/O device 812 can be analogous to the multi-touch sensing surface described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1.

In examples for which touch I/O device 812 is a touch screen, the touch screen can use liquid crystal display (LCD) technology, light emitting polymer display (LPD) technology, organic LED (OLED), or organic electro luminescence (OEL), although other display technologies can be used in other examples.

Feedback can be provided by touch I/O device 812 based on the user's touch input as well as a state or states of what is being displayed and/or of the computing system. Feedback can be transmitted optically (e.g., light signal or displayed image), mechanically (e.g., haptic feedback, touch feedback, force feedback, or the like), electrically (e.g., electrical stimulation), olfactory, acoustically (e.g., beep or the like), or the like or any combination thereof and in a variable or non-variable manner.

System architecture 800 can also include power system 844 for powering the various hardware components and can include a power management system, one or more power sources, a recharging system, a power failure detection circuit, a power converter or inverter, a power status indicator and any other components typically associated with the generation, management and distribution of power in portable devices.

In some examples, peripherals interface 816, one or more processors 818, and memory controller 820 of the processing system 804 can be implemented on a single chip. In some other examples, they can be implemented on separate chips.

Therefore, according to the above, some examples of the disclosure are directed to a device for determining a heart rate of a user. The device can comprise a sensor configured to generate first signals when positioned on or adjacent to a user's skin, an accelerometer configured to generate one or more acceleration signals and processing circuitry capable of removing, in a time domain, motion artifacts from the first signals based on the acceleration signals to determine the heart rate. Additionally or alternatively to one or more of the examples disclosed above, the processing circuitry can be further capable of generating one or more integrated acceleration signals from the one or more acceleration signals and removing motion artifacts from the first signals based on the acceleration signals and the integrated acceleration signals. Additionally or alternatively to one or more of the examples disclosed above, the one or more integrated acceleration signals can be mean-centered and scaled to have a variance matching the one or more acceleration signals used to generate the corresponding integrated acceleration signals. Additionally or alternatively to one or more of the examples disclosed above, the processing circuitry can be further capable of removing motion artifacts using a least squares algorithm to identify a best representation of acceleration and integrated acceleration signals in the first signals. Additionally or alternatively to one or more of the examples disclosed above, the processing circuitry can be further capable of: projecting the acceleration and integrated acceleration signals and generating residual first signals based on the projected acceleration and integrated acceleration signals and the first signals. Additionally or alternatively to one or more of the examples disclosed above, the processing circuitry can be further capable of: generating latent variables for the acceleration and integrated acceleration signals, projecting one or more components of the generated latent variables, and generating residual heart rate signals based on the projected one or more components of the generated latent variables and the heart rate signals. Additionally or alternatively to one or more of the examples disclosed above, the processing circuitry can be further capable of: generating first latent variables for the acceleration and integrated acceleration signals during a first iteration; projecting one or more components of the first latent variables generated during the first iteration; generating first residual heart rate signals based on the projected one or more components of the first latent variables generated during the first iteration and the heart rate signals; deflating the acceleration and integrated acceleration signals based on the projected one or more components of the latent variable generated during the first iteration; generating second latent variables for the deflated acceleration and integrated acceleration signals during a second iteration; projecting one or more components of the second latent variables generated during the second iteration; and generating second residual heart rate signals based on the projected one or more components of the second latent variables generated during the second iteration and the first residual heart rate signals. Additionally or alternatively to one or more of the examples disclosed above, the processing circuitry can be further capable of: removing motion artifacts based on heart signals and acceleration signals from a plurality of overlapping time intervals to generate a plurality of overlapping residual first signals and generating a final time domain heart rate signal by averaging the plurality of overlapping first signals for the time intervals. Additionally or alternatively to one or more of the examples disclosed above, the processing circuitry can be further capable of determining at least one of an instantaneous heart rate, heart rate variability or average heart rate based on the first signals after removing motion artifacts.

Some examples of the disclosure are directed to a method executed by processing circuitry for determining a heart rate of a user. The method can comprise receiving first signals generated by a sensor when positioned on or adjacent to a user's skin, receiving acceleration signals generated by an accelerometer, and removing, in a time domain, motion artifacts from the first signals based on the acceleration signals to determine the heart rate. Additionally or alternatively to one or more of the examples disclosed above, the method can further comprise: generating one or more integrated acceleration signals from the one or more acceleration signals and removing motion artifacts from the first signals based on the acceleration signals and the integrated acceleration signals. The one or more integrated acceleration signals can be mean-centered and scaled to have a variance matching the one or more acceleration signals used to generate the corresponding integrated acceleration signals. Additionally or alternatively to one or more of the examples disclosed above, the method can further comprise: projecting the acceleration and integrated acceleration signals, and generating residual heart rate signals based on the projected acceleration and integrated acceleration signals and the first signals. Additionally or alternatively to one or more of the examples disclosed above, the method can further comprise: generating latent variables for the acceleration and integrated acceleration signals, projecting one or more components of the generated latent variables, and generating residual heart rate signals based on the projected one or more components of the generated latent variables and the first signals. Additionally or alternatively to one or more of the examples disclosed above, the method can further comprise: generating first latent variables for the acceleration and integrated acceleration signals during a first iteration; projecting one or more components of the first latent variables generated during the first iteration; generating first residual heart rate signals based on the projected one or more components of the first latent variables generated during the first iteration and the first signals; deflating the acceleration and integrated acceleration signals based on the projected one or more components of the latent variable generated during the first iteration; generating second latent variables for the deflated acceleration and integrated acceleration signals during a second iteration; projecting one or more components of the second latent variables generated during the second iteration; and generating second residual heart rate signals based on the projected one or more components of the second latent variables generated during the second iteration and the first residual heart rate signals. Additionally or alternatively to one or more of the examples disclosed above, the first signals and acceleration signals from a plurality of overlapping time intervals can be used to generate a plurality of overlapping residual heart rate signals, and the method can further comprise: generating a final time domain heart rate signal by averaging the plurality of overlapping heart rate signals for the time intervals. Additionally or alternatively to one or more of the examples disclosed above, the method can further comprise: measuring a time separation between two peaks in the first signals, and determining an instantaneous heart rate based on the time separation between two peaks. Additionally or alternatively to one or more of the examples disclosed above, the method can further comprise: measuring a time separation between a plurality of peaks in the first signals, determining instantaneous heart rates based on the time separation between adjacent peaks of the plurality of peaks, and determining heart rate variability based on the determined instantaneous heart rates. Additionally or alternatively to one or more of the examples disclosed above, the method can further comprise: measuring a number of peaks in the first signals during a time interval and determining an average heart rate based on the number of peaks in the first signals during the time interval.

Some examples of the disclosure are directed to a non-transitory computer readable storage medium. The computer readable medium can contain instructions that, when executed, can perform a method for operating an electronic device, the electronic device including a processor. The method can comprise: receiving first signals generated by a sensor when positioned on or adjacent to a user's skin, receiving acceleration signals generated by an accelerometer, and removing, in a time domain, motion artifacts from the first signals based on the acceleration signals to determine the heart rate. Additionally or alternatively to one or more of the examples disclosed above, the method can further comprise: generating one or more integrated acceleration signals from the one or more acceleration signals and removing motion artifacts from the first signals based on the acceleration signals and the integrated acceleration signals. The one or more integrated acceleration signals can be mean-centered and scaled to have a variance matching the one or more acceleration signals used to generate the corresponding integrated acceleration signals. Additionally or alternatively to one or more of the examples disclosed above, the method can further comprise: projecting the acceleration and integrated acceleration signals, and generating residual heart rate signals based on the projected acceleration and integrated acceleration signals and the first signals. Additionally or alternatively to one or more of the examples disclosed above, the method can further comprise: generating latent variables for the acceleration and integrated acceleration signals, projecting one or more components of the generated latent variables, and generating residual heart rate signals based on the projected one or more components of the generated latent variables and the first signals. Additionally or alternatively to one or more of the examples disclosed above, the method can further comprise: generating first latent variables for the acceleration and integrated acceleration signals during a first iteration; projecting one or more components of the first latent variables generated during the first iteration; generating first residual heart rate signals based on the projected one or more components of the first latent variables generated during the first iteration and the first signals; deflating the acceleration and integrated acceleration signals based on the projected one or more components of the latent variable generated during the first iteration; generating second latent variables for the deflated acceleration and integrated acceleration signals during a second iteration; projecting one or more components of the second latent variables generated during the second iteration; and generating second residual heart rate signals based on the projected one or more components of the second latent variables generated during the second iteration and the first residual heart rate signals. Additionally or alternatively to one or more of the examples disclosed above, the first signals and acceleration signals from a plurality of overlapping time intervals can be used to generate a plurality of overlapping residual heart rate signals, and the method can further comprise generating a final time domain heart rate signal by averaging the plurality of overlapping heart rate signals for the time intervals. Additionally or alternatively to one or more of the examples disclosed above, the method can further comprise: determining at least one of an instantaneous heart rate, heart rate variability or average heart rate based on the first signals after removing motion artifacts.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

The invention claimed is:

1. A device for determining a heart rate of a user, comprising:
   a light emitter operative to emit light towards a skin of the user when the device is worn by the user;
   a light detector operative to receive a portion of the emitted light that has interacted with the skin of the user and generate a light signal corresponding to the received portion of the emitted light;
   an accelerometer operative to generate an acceleration signal corresponding to a movement of the user, wherein the acceleration signal comprises a signal stream of acceleration measurements; and
   a processor operative to:
      receive the light signal and the acceleration signal;
      generate an integrated acceleration signal from the acceleration signal;
      identify, using a least squares algorithm, a best representation of the acceleration signal and the integrated acceleration signal in the light signal;
      remove the identified best representation of the acceleration signal and the integrated acceleration signal from the light signal to generate a filtered signal; and
      determine the heart rate of the user using the filtered signal.

2. The device of claim 1, wherein the integrated acceleration signal comprises a cumulative sum of the acceleration measurements of an accelerometer axis.

3. The device of claim 1, wherein the integrated acceleration signal is mean-centered and scaled to have a variance matching a variance of the acceleration signal.

4. The device of claim 1, wherein the processor is configured to:
   establish a sampling window comprising a fixed number of light signal samples;
   identify acceleration samples from the acceleration signal that correspond to the fixed number of light samples; and
   determine the heart rate using light samples and acceleration samples included in the sampling window.

5. The device of claim 4, wherein:
   the sampling window is a first sampling window; and
   the processor is configured to:
      establish of a plurality of overlapping sampling windows; and
      determine the heart rate using the plurality of overlapping sampling windows to determine an instantaneous heart rate, a heart rate variability or a combination thereof.

6. A device for determining a heart rate of a user, comprising:
   a light emitter operative to emit light;
   a light detector operative to receive a portion of the emitted light that has interacted with a skin of the user and generate a light signal corresponding to the received portion of the emitted light;
   an accelerometer that is operative to generate acceleration signals, the acceleration signals comprising:
      a first acceleration signal having a first stream of acceleration measurements corresponding to a first accelerometer axis; and
      a second acceleration signal having a second stream of acceleration measurements corresponding to a second accelerometer axis; and
   a processor operative to:
      generate integrated acceleration signals, the integrated acceleration signals comprising a first integrated acceleration signal generated from the first acceleration signal and a second integrated acceleration signal generated from the second acceleration signal;
      identify, using a least squares algorithm, a best representation of the acceleration signals and the integrated acceleration signals in the light signal;
      remove the identified best representation of the acceleration signals and the integrated acceleration signals from the light signal to generate a residual signal; and
      determine the heart rate of the user based on the residual signal.

7. The device of claim 6, wherein the processor is operative to:
   generate latent variables for the acceleration signals and the one or more integrated acceleration signals; and
   identify the best representation of the acceleration signals and the integrated acceleration signals based on the generated latent variables.

8. The device of claim 6, wherein determining the heart rate comprises determining at least one of an instantaneous heart rate, a heart rate variability, an average heart rate, or a combination thereof based on the light signal with the motion artifact removed.

9. The device of claim 6, wherein:
   the acceleration signals further comprise a third acceleration signal having a third stream of acceleration measurements corresponding to a third accelerometer axis; and
   the processor is operative to remove the motion artifact from the light signal using the first, second, and third acceleration signals.

10. The device of claim 9, wherein the integrated acceleration signals comprises a third integrated acceleration signal from the third acceleration signal.

11. The device of claim 6, wherein the processor is configured to:
   establish a sampling window comprising a fixed number of light signal samples;
   identify acceleration samples from the first acceleration signal and second acceleration signal that correspond to the fixed number of light samples; and
   determine the heart rate of the user over the sampling window.

12. The device of claim 11, wherein:
   the sampling window is a first sampling window; and
   the processor is configured to:
      establish of a plurality of overlapping sampling windows; and
      determine the heart rate using the plurality of overlapping sampling windows to determine an instantaneous heart rate, a heart rate variability or a combination thereof.

13. A method for determining a heart rate of a user, the method comprising:
   emitting light from a light emitter and toward a skin of the user;

detecting a portion of the light that has interacted with the skin of the user;

generating a light signal indicative of the detected portion of the emitted light;

generating, using an accelerometer, an acceleration signal corresponding to movement of the user;

generating an integrated acceleration signal from the acceleration signal;

identifying, using a least squares algorithm, a best representation of the acceleration signal and the integrated acceleration signal, in the light signal;

removing the identified best representation of the acceleration signal and the integrated acceleration signal from the light signal to generate a residual signal; and determining the heart rate of the user using the residual signal.

14. The method of claim 13, wherein determining the heart rate comprises determining at least one of an instantaneous heart rate, a heart rate variability, an average heart rate, or a combination thereof based on the light signal with the motion artifacts removed.

\* \* \* \* \*